(12) United States Patent
Darwin et al.

(10) Patent No.: US 7,282,491 B2
(45) Date of Patent: Oct. 16, 2007

(54) **PROKARYOTIC PROTEASOMAL PROTEASES OF *MYCOBACTERIUM TUBERCULOSIS* (MTB) AS TARGETS FOR ANTIBIOTIC THERAPY**

(75) Inventors: Katerina Heran Darwin, New York, NY (US); Carl F. Nathan, Larchmont, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 119 days.

(21) Appl. No.: 10/730,555

(22) Filed: Dec. 8, 2003

(65) Prior Publication Data

US 2004/0213776 A1    Oct. 28, 2004

Related U.S. Application Data

(60) Provisional application No. 60/431,676, filed on Dec. 2, 2002, provisional application No. 60/471,774, filed on May 19, 2003.

(51) Int. Cl.
*A61K 31/12* (2006.01)
*A61K 31/69* (2006.01)

(52) U.S. Cl. .................... 514/64; 514/675; 630/250
(58) Field of Classification Search .................... None
See application file for complete search history.

(56) References Cited

OTHER PUBLICATIONS

Schubert et al., Proteasome inhibition interferes with Gag polyprotein processing, release, and maturation of HIV-1 and HIV-2, Nov. 2000, PNAS, vol. 97, pp. 13057-13062.*

J. Adams, 2002, "Proteasome inhibitors as new anticancer drugs", Current Opinion in Oncology, vol. 14, pp. 626-634.*
Bair et al., 2001, "Structures of coenzyme F240 in Mycobacterium species", Archives of Microbiology, vol. 176, pp. 37-43.*
Baumeister et al., 1998, "The proteasome: paradigm of a self-compartmentalizing protease", Cell, vol. 92, pp. 367-380.*
Elofsson et al., 1999, "Towards subunit-specific proteasome inhibitors: synthesis and evaluation of peptide [alpha[,[beta]-epoxyketones", Chemistry & Biology, vol. 6, pp. 811-822.*
Freidberg et al., Eds., 1995, "Nucleotide excision repair in prokaryotes", in DNA Repair and Mutagenesis, ASM Press, pp. 191-232.*
Isabelle et al., 2002, "Large-scale production of Coenzyme F420-5,6 using *Mycobacteriaum smegmatis*", Applied and Environmental Microbiology, vol. 68, pp. 5750-5755.*

(Continued)

*Primary Examiner*—Nashaat T. Nashed
*Assistant Examiner*—William W. Moore
(74) *Attorney, Agent, or Firm*—Nixon Peabody LLP

(57) ABSTRACT

The present invention relates to methods of treating *Mycobacterium* pathogen infection in a subject that involve: inhibiting proteasomal activity in a pathogen under conditions effective to make the pathogen susceptible to antibacterial host defenses; inhibiting enzyme activity in a pathogen under conditions effective to make the pathogen susceptible to antibacterial host defenses, where the enzyme is a DNA repair enzyme or a flavin-like co-factor synthesis enzyme, or inhibiting proteasomal and enzyme activity under conditions to make the pathogen susceptible to antibacterial host defenses. The present invention also relates to methods for screening compounds that inhibit proteasomal and protease activity, DNA repair enzyme activity, or flavin-like co-factor synthesis enzyme activity, where the inhibitory compounds have an ability to sensitize bacteria to the antibacterial effects of oxidative/nitrosative stress.

12 Claims, 15 Drawing Sheets

OTHER PUBLICATIONS

Lowe et al., 1995, "Crystal structure of the 20S proteasome from the archaeon *T. acidophilum* at 3.4A resolution", Science, vol. 268, pp. 533-539.*

Lu et al., 2002, "The global regulator ArcA controls resistance to reactive nitrogen and oxygen intermediates in *Salmonella enterica* serovar Enteritidis", Infection and Immunity, vol. 70, pp. 451-461.*

Lupas et al., 1997, "Eubacterial proteasomes", Molecular Biology Reports, 24: 125-131.*

Nagy et al., 1997, "Further sequence analysis of the DNA regions with the Rhodococcus 20S proteasome structural genes reveals extensive homology *Mycobacterium leprae*", DNA Sequence, vol. 7, pp. 225-228.*

Orren et al., 1992, "Post-incision steps of nucleotide excision repair in *Escherichia coli*", The Journal of Biological Chemistry, vol. 267, pp. 780-788.*

A. Sancar, 1996, "DNA excision repair", in Annual Review of Biochemistry, vol. 65, pp. 43-81.*

Skorvaga et al., 2002, The [beta]-hairpin motif of UvrB is essential for DNA binding, damage processing and UvrC-mediated incisions, The Journal of Biological Chemistry, vol. 277, pp. 1553-1559.*

R. H. White, 2001, "Biosynthesis of the methanogenic cofactors", in Vitamins & Hormones, vol. 61, pp. 299-337.*

Akaike, "Role of Free Radicals in Viral Pathogenesis and Mutation," *Rev. Med. Virol.* 11(2):87-101 (2001).

Bloom et al., "Tuberculosis: Commentary on a Re-Emergent Killer," *Science* 257:1055-1064 (1992).

Benaroudj et al., "PAN, the Proteasome-Activating Nucleotidase from Archaebacteria, is a Protein-Unfolding Molecular Chaperone," *Nat. Cell. Biol.* 2(11):833-839 (2000).

Bryk et al., "Metabolic Enzymes of Mycobacteria Linked to Antioxidant Defense by a Thioredoxin-Like Protein," *Science* 295(5557):1037-1077 (2002).

Buchmeier et al., "A Parallel Intraphagosomal Survival Strategy Shared by *Mycobacterium tuberculosis* and *Salmonella enterica*," *Molec. Microbiol.* 35(6):1375-1382 (2000).

Chan et al., "Killing of Virulent *Mycobacterium tuberculosis* by Reactive Nitrogen Intermediates Produced by Activated Murine Macrophages," *J. Exp. Med.* 175:1111-1122 (1992).

Chan et al., "Effects of Nitric Oxide Synthase Inhibitors on Murine Infection with *Mycobacterium tuberculosis*," *Infect Immun.* 63(2):736-740 (1995).

Choi et al., "Demonstration that *fbiC* is required by *Mycobacterium bovis* BCG for Coenzyme $F_{420}$ and FO Biosynthesis," *J. Bacteriol.* 184(9):2420-2428 (2002).

Cole et al., "Massive Gene Decay in the Leprosy Bacillus," *Nature* 409:1007-1011 (2001).

Daley et al., "An Outbreak of Tuberculosis with Accelerated Progression Among Persons Infected with the Human Immunodeficiency Virus. An Analysis Using Restriction-Fragment-Length Polymorphisms," *N. Engl. J. Med.* 326(4):231-235 (1992).

Davies K.J., "Degradation of Oxidized Proteins by the 20S Proteasome," *Biochimie* 83:301-310 (2001).

De Mot et al., "Proteasomes and Other Self-Compartmentalizing Proteases in Prokaryotes," *Trends Microbiol.* 7(2):88-92 (1999).

Dye et al., "Consensus Statement. Global Burden of Tuberculosis: Estimated Incidence, Prevalence, and Mortality by Country. WHO Global Surveillance and Monitoring Project," *JAMA* 282(7):677-686 (1999).

Ehrt et al., "Reprogramming of the Macrophage Transcriptome in Response to Interferon-γ and *Mycobacterium tuberculosis*: Signaling roles of Nitric Oxide Synthase-2 and Phagocyte Oxidase," *J. Exp. Med.* 194(8):1123-1140 (2001).

Facchetti et al., "Expression of Inducible Nitric Oxide Synthase in Human Granulomas and Histiocytic Reactions," *Am. J. Pathol.* 154(1):145-152 (1999).

Forbes et al., "Divalent-Metal Transport by NRAMP Proteins at the Interface of Hose-Pathogen Interactions," *Trends Microbiol.* 9(8):397-403 (2001).

Graham et al., "Identification of *Mycobacterium tuberculosis* RNAs Synthesized in Response to Phagocytosis by Human Macrophages by Selective Capture of Transcribed Sequences (SCOTS)," *Proc. Natl. Acad. Sci. USA* 96:11554-11559 (1999).

Grune et al., "Peroxynitrite Increases the Degradation of Aconitase and Other Cellular Proteins by Proteasome," *J. Biol. Chem.* 273(18):10857-10862 (1998).

Hernandez-Pando et al., "Persistence of DNA from *Mycobacterium tuberculosis* in Superficially Normal Lung Tissue During Latent Infection," *Lancet* 356:2133-2138 (2000).

Karimova et al., "A Bacterial Two-Hybrid System Based on a Reconstituted Signal Transduction Pathway," *Proc. Natl. Acad. Sci. USA* 95:5752-5756 (1998).

Kaushal et al., "Reduced Immunopathology and Mortality Despite Tissue Persistence in a *Mycobacterium tuberculosis* Mutant Lacking Alternative σ Factor, SigH," *Proc. Natl. Acad. Sci. USA* 99(12):8330-8335 (2002).

Keane et al., "Tubercuolosis Associated with Infliximab, a Tumor Necrosis-Factor α-Neutralizing Agent," *N. Engl. M. Med.* 345(15):1098-1104 (2001).

Kisselev et al., "Proteasome Inhibitors: from Research Tools to Drug Candidates," *Chem. Biol.* 8(8):739-758 (2001).

Knipfer et al., "Inactivation of the 20S Proteasome in *Mycobacterium smegmatis*," *Mol. Microbiol.* 25(2):375-383 (1997).

Langer, T. "AAA Proteases: Cellular Machines for Degrading Membrane Proteins," *Trends in Biol. Sci.* 25:247-251 (2000).

Lienhardt et al., Estimation of the Impact of the Human Immunodeficiency Virus Infection on Tuberculosis: Tuberculosis Risks Re-visited? *Int. J. Tuberc. Lung Dis.* 1(3):196-203 (1997).

Long et al., "Mycobacteriocidal Action of Exogenous Nitric Oxide," *Antimicrob. Agents Chemother.* 43(2):403-405 (1999).

MacMicking et al., "Altered Responses to Bacterial Infection and Endotoxic Shock in Mice Lacking Inducible Nitric Oxide Synthase," *Cell* 81:641-650 (1995).

MacMicking et al., "Nitric Oxide and Macrophage Function," *Annu. Rev. Immunol.* 15:323-350 (1997).

MacMicking et al., "Identification of Nitric Oxide Synthase as a Protective Locus Against Tuberculosis," *Proc. Natl. Acad. Sci. USA* 94:5243-5248 (1997).

Manganelli et al., "Role of the Extracytoplasmic-Function Sigma Factor Sigma(H) in *Mycobacterium tuberculosis* Global Gene Expression," *Mol. Microbiol.* 45(2):365-374 (2002).

Maragos et al., "Mutagenicity of Glyceryl Trinitrate (nitroglycerin) in *Salmonella typhimurium*," *Mutat. Res.* 298(3):187-195 (1993).

Mogues et al., "The Relative Importance of T Cell Subsets in Immunity and Immunopathology of Airborne *Mycobacterium tuberculosis* Infection in Mice," *J. Exp. Med.* 193(3):271-280 (2001).

Nagy et al., "The 20S Proteasome of *Streptomyces coelicolor*," *J. Bacteriol.* 180(20):5448-5453 (1998).

Nakata et al., "*Mycobacterium Tuberculosis* Enhances Human Immunodeficiency Virus-1 Replication in the Lung," *Am. J. Resp. & Crit. Care Med.* 155:996-1003 (1997).

Nathan et al., "Reactive Oxygen and Nitrogen Intermediates in the Relationship Between Mammalian Hosts and Microbial Pathogens," *Proc. Natl. Acad. Sci. USA* 97(16):8841-8848 (2000).

Nathan et al., "Inducible Nitric Oxide Synthase in the Tuberculous Human Lung," *Am. J. Respir. Crit. Care Med.* 166:130-131 (2002).

Nathan et al., in *In Tubercolosis, Second Edition*, Rom et al., eds., Lippincott Williams & Wilkins, New York, New York, pp. 215-235 (2003).

Ogura et al., "AAA Superfamily ATPases; Common Structure-Diverse Function," *Genes to Cells* 6:575-97 (2001).

Raman et al., "The Alternative Sigma Factor SigH Regulates Major Components of Oxidative and Heat Stress Responses in *Mycobacterium tuberculosis*," *J. Bacteriol.* 183(20):6119-6125 (2001).

Raupach et al., "Immune Responses to Intracellular Bacteria," *Curr. Opin. Immun.* 13:417-428 (2001).

Rosenkrands et al., "Towards the Proteome of *Mycobacterium tuberculosis*," *Electrophoresis* 21:3740-3756 (2000).

Russell, "*Mycobacterium tuberculosis*: Here Today, and Here Tomorrow," *Nat. Rev. Mol. Cell. Biol.* 2:569-577 (2001).

Sassetti et al., "Comprehensive Identification of Conditionally Essential Genes in Mycobacteria," *Proc. Natl. Acad. Sci. USA* 98(22):12712-12717 (2001).

Sassetti et al., "Genes Required for Mycobacterial Growth Defined by High Density Mutagenesis," *Mol. Microbiol.* 48(1):77-84 (2003).

Scanga et al., "The Inducible Nitric Oxide Synthase Locus Confers Protection Against Aerogenic Challenge of Both Clinical and Laboratory Strains of *Mycobacterium tuberculosis* in Mice," *Infect. Immun.* 69(12):7711-7717 (2001).

Schaible et al., "Cytokine Activation Leads to Acidification and Increases Maturation of *Mycobacterium avium*-Containing Phagosomes in Murine Macrophages," *J. Immunol.* 160(3):1290-1296 (1998).

St. John et al., "Peptide Methionine Sulfoxide Reductase from *Escherichia coli* and *Mycobacterium tuberculosis* Protects Bacteria Against Oxidative Damage from Reactive Nitrogen Intermediates," *Proc. Natl. Acad. Sci. USA* 98(17):9901-9906 (2001).

Stuehr et al., "Nitric Oxide. A Macrophage Product Responsible for Cytostasis and Respiratory Inhibition in Tumor Target Cells," *J. Exp. Med.* 169:1543-1555 (1989).

Tamir et al., "DNA Damage by Nitric Oxide," *Chem. Res. Toxicol.* 9(5):821-7 (1996).

Theis et al., "The Nucleotide Excision Repair Protein UvrB, a Helicase-Like Enzyme with a Catch," *Mutat. Res.* 460:277-300 (2000).

Vale, RD. "AAA proteins: Lords of the Ring," *J. Cell Biol* 150(1):F13-19 (2000).

Walter S., "Structure and Function of the GroE Chaperone," *Cell. Mol. Life Sci.* 59:1589-1597 (2002).

Wolf et al., "Characterization of ARC, a Divergent Member of the AAA ATPase Family from *Rhodococcus erythropolis*," *J. Mol. Biol.* 277(1):13-25 (1998).

Weber et al., "Anaerobic nitrate Reductase (narGHJI) Activity of *Mycobacterium bovis* BCG in vitro and its Contribution to Virulence in Immunodeficient Mice," *Mol. Micro.* 35(5):1017-1025 (2000).

Whalen et al., "Accelerated Course of Human Immunodeficieny Virus Infection after Tuberculosis.," *Am. J. Resp. & Crit. Care Med.* 151:129-135 (1995).

World Health Organization, "Tuberculosis and AIDS: Statement on AIDS and Tuberculosis," *Bulletin Int. Tuber. Lung Dis* 64(1):8-11 (1989).

Zhuang et al., "Nitric Oxide-Induced Mutations in the HPRT Gene of Human Lymphoblastoid TK6 Cells and in *Salmonella typhimurium*," *Environ. Mol. Mutagen.* 35(1):39-47 (2000).

Zhuang et al., "Mutagenesis Associated with Nitric Oxide Production in Macrophages," *Proc. Natl. Acad. Sci. USA* 95:8286-8291 (1998).

Cole et al., "Deciphering the Biology of *Mycobacterium tuberculosis* from the Complete Genome Sequence," *Nature* 393:537-544 (1998).

Cole et al., "Deciphering the Biology of *Mycobacterium tuberculosis* from the Complete Genome Sequence," Erratum in: *Nature* 396:190-198 (1998).

\* cited by examiner

Pool 64 NO2 d3 sub d16 1/4/02

|   | 1 | 2 | 3 | 4 | 5 | 6 | 7 | 8 | 9 | 10 | 11 | 12 |
|---|---|---|---|---|---|---|---|---|---|---|---|---|
| A |  |  |  |  |  |  |  |  |  |  |  |  |
| B | -0.001 | 0.466 | 0.432 | 0.306 | 0.548 | 0.336 | 0.326 | 0.361 | 0.447 | 0.416 | 0.369 |  |
| C | 0.001 | 0.466 | 0.346 | 0.284 | 0.337 | 0.292 | 0.281 | 0.225 | 0.383 | 0.219 | 0.496 |  |
| D | 0.000 | 0.446 | 0.264 | 0.338 | 0.357 | 0.427 | 0.211 | 0.327 | 0.441 | 0.364 | 0.249 |  |
| E |  | 0.371 | 0.389 | 0.244 | 0.267 | 0.135 | 0.359 | 0.330 | 0.301 | 0.258 | 0.348 |  |
| F |  | 0.095 | 0.437 | 0.406 | 0.360 | 0.422 | 0.456 | 0.290 | 0.260 | 0.235 | 0.241 |  |
| G |  | 0.350 | 0.272 | 0.001 | 0.376 | 0.380 | 0.436 | 0.374 | 0.358 | 0.462 | 0.412 |  |
| H |  |  |  |  |  |  |  |  |  |  |  |  |

Endpoint
Lm1 580
Automix: Off
Calibrate: On

Plate Last Read:
1:13 AM 1/4/02

Wavelength Combination: !Lm1
Data Mode: Absorbance
Plate Blank Used Lm1 = 0.085

FIG. 1

PROKARYOTIC PROTEASOMAL PROTEASES OF MYCOBACTERIUM TUBERCULOSIS (MTB) AS TARGETS FOR ANTIBIOTIC THERAPY

This application claims the benefit of U.S. Provisional Patent Application Ser. No. 60/431,676, filed Dec. 6, 2002, and U.S. Provisional Patent Application Ser. No. 60/471,774, filed May 19, 2003.

This invention was developed with government funding by the National Institutes of Health Grant No. HL61241 and National Institutes of Health Immunology Training Grant No. T32 A107621. The U.S. Government may have certain rights.

FIELD OF THE INVENTION

The present invention relates to methods of treating pathogenic infection in mammals.

BACKGROUND OF THE INVENTION

About two billion people are thought to be infected with the bacillus *Mycobacterium tuberculosis* ("Mtb"), the causative agent of *tuberculosis* ("TB"). The majority of those infected do not show signs of disease; however, each year about 8 million individuals develop active *tuberculosis* and about 2 million die (Dye et al., "Consensus Statement. Global Burden of *Tuberculosis*: Estimated Incidence, Prevalence, and Mortality by Country. WHO Global Surveillance and Monitoring Project," *JAMA* 282(7):677-86 (1999)). Cure of *tuberculosis* requires months of treatment with multiple anti-infective agents. Incomplete treatment is common and encourages the emergence of multi-drug resistant ("MDR") strains. MDR isolates are detected in all nations and prevalent in some. Infection can be acquired by sharing airspace with an individual with cavitary disease, with an infectious dose estimated at 1-10 inhaled *bacilli*.

Furthermore, Mtb is a bioterrorism threat, because it has high potential for generating public fear and economic disruption. Bioterrorists could send individuals with cavitary MDR-TB through mass transit networks. Although few of the people exposed would ever develop TB, and almost none would be sickened acutely, knowledge would spread that many of those exposed would be likely to become infected, and that if MDR-TB did develop, it would be difficult to treat and lethal in up to 35% of cases among otherwise healthy individuals, even given optimal care. This would discourage congregation in subways, buses, train stations, and airports, causing economic disruption. Even a handful of cases of MDR-TB could overwhelm a regional hospital system's capacity to provide isolation. The disease rate is low, but the infection rate is high when organisms are aerosolized in shared space. Aerosolization requires no technology, only coughing.

Mtb infection can persist for decades (World Health Organization, "*Tuberculosis* and AIDS: Statement on AIDS and *Tuberculosis,*" *Bull. Int. Tuberc. Lung Dis.* 64:88-111 (1989); Bloom et al., "*Tuberculosis*: Commentary on a Re-Emergent Killer," *Science* 257:55-64 (1992); Russell, "*Mycobacterium Tuberculosis*: Here Today, and Here Tomorrow," *Nat. Rev. Mol. Cell. Biol.* 2:1-9 (2001); Raupach et al., "Immune Responses to Intracellular Bacteria," *Curr. Opin. Imm.* 13:417-428 (2001)). The normal immune system creates an environment in which Mtb is not completely sterilized, yet replicates so little that 90% of immune-competent hosts who are infected with Mtb never develop overt TB. During latent infection, the primary residence of Mtb is the macrophage. The antimicrobial arsenal of the activated macrophage includes inducible NO synthase ("iNOS" or "NOS2"). At the acidic pH (<5.5) prevalent in the phagosome of activated macrophages (Schaible et al., "Cytokine Activation Leads to Acidification and Increases Maturation of *Mycobacterium* Avium-Containing Phagosomes in Murine Macrophages," *J. Immunol.* 160(3):1290-1296 (1998)), nitrite, a major oxidation product of NO, is partially protonated to nitrous acid, which dismutates to form NO and another radical, $NO_2$ (Stuehr et al., "Nitric Oxide. A Macrophage Product Responsible for Cytostasis and Respiratory Inhibition in Tumor Target Cells," *J.Exp. Med.* 169(5):1543-1555 (1989)). Thus, mildly acidified nitrite is a physiologic antimicrobial system. Reactive nitrogen intermediates ("RNI") may inflict not only nitrosative but also oxidative injury, as when NO combines with superoxide from bacterial metabolism to generate peroxynitrite within the bacterium (St John et al., "Peptide Methionine Sulfoxide Reductase from *Escherichia coli* and *Mycobacterium Tuberculosis* Protects Bacteria Against Oxidative Damage from Reactive Nitrogen Intermediates," *Proc. Natl. Acad. Sci. USA* 98(17): 9901-9906 (2001)). Reagent NO kills Mtb with a molar potency exceeding that of most anti-*tuberculosis* drugs (Long et al., "Mycobacteriocidal Action of Exogenous Nitric Oxide," *Antimicrob. Agents Chemother.* 43(2):403-405 (1999), Nathan et al., in *In Tuberculosis,* Second Edition, Rom et al., eds., Lippincott Williams & Wilkins, New York, N.Y., pp. 215-235 (2003)). In humans and mice with *tuberculosis,* macrophages in infected tissues and airways express enzymatically active iNOS (Facchetti et al., "Expression of Inducible Nitric Oxide Synthase in Human Granulomas and Histiocytic Reactions," *Am. J. Pathol.* 154(1):145-52 (1999), Nathan, "Inducible Nitric Oxide Synthase in the *Tuberculous* Human Lung," *Am. J. Respir. Crit. Care Med.* 166(2):13-131 (2002), Schon, Dissertation, No. 749, *Linköping Universitet* (2002)). Mice lacking iNOS cannot control Mtb infection (MacMicking et al., "Identification of Nitric Oxide Synthase as a Protective Locus Against *Tuberculosis,*" *Proc. Natl Acad. Sci. USA* 94(10):5243-5248 (1997)). Despite the protective effects of RNI, a small number of viable *mycobacteria* usually persist for the lifetime of the infected host (Hemandez-Pando et al., "Persistence of DNA from *Mycobacterium Tuberculosis* in Superficially Normal Lung Tissue During Latent Infection," *Lancet* 356(9248):2133-2138 (2000)), and sometimes resume growth.

Persistence of Mtb in those lacking overt disease is evidenced by the emergence of TB in patients with arthritis or Crohn's disease immunosuppressed by biologicals that neutralize TNF (Keane et al., "*Tuberculosis* Associated with Infliximab, a Tumor Necrosis-Factor α-Neutralizing Agent," *N. Engl. M. Med.* 345: 1098-1104 (2001)). More significantly, emergence of overt TB in people with subclinical Mtb infection reaches 50-80% with supervening HIV disease. Worldwide, TB may be the leading cause of death in AIDS patients (World Health Organization, "*Tuberculosis* and AIDS: Statement on AIDS and *Tuberculosis,*" *Bull. Int. Tuberc. Lung Dis.* 64:88-111 (1989); Bloom et al., "*Tuberculosis*: Commentary on a Re-Emergent Killer," *Science* 257:55-64 (1992); Daley et al., "An Outbreak of *Tuberculosis* with Accelerated Progression Among Persons Infected with the Human Immunodeficiency Virus. An Analysis Using Restriction-Fragment-Length Polymorphisms," *N. Engl. J. Med.* 326:231-235 (1992); and Lienhardt et al., "Estimation of the Impact of the Human Immunodeficiency Virus Infection on *Tuberculosis: Tuberculosis* Risks Re-visited? *Int. J. Tuberc. Lung Dis.* 1:196-204 (1997)), and TB exacerbates growth of HIV (Whalen et al., "Accelerated Course of Human Immunodeficiency Virus Infection after *Tuberculosis.*," *Am. J. Resp. & Crit. Care Med.* 151:129-135 (1995); and Nakata et al., "*Mycobacterium Tuberculosis* Enhances Human Immunodeficiency Virus-1 Replication in the Lung," *Am. J. Resp. & Crit. Care Med.* 155:996-1003 (1997)). Lifelong persistence of infection in immunocompetent hosts and exacerbation of infection in immunodeficient hosts suggest a dynamic balance. Inhibition of Mtb resistance pathways might tilt the balance in favor of the host, allowing the host to sterilize the pathogen and perhaps allowing conventional chemotherapy to kill the pathogen faster. Inhibition of the pathways by which Mtb resists the host might allow people who are subclinically infected to rid themselves of persistent *bacilli,* reduce their lifelong risk of reactivation TB, and interrupt the pandemic.

Among the most successful forms of anti-Mtb chemotherapy is that applied naturally by the host. Of these, nitric oxide ("NO") is the only molecule known to be produced by mammalian cells that can kill tubercle *bacilli* in vitro with a potency (~150 nM) comparable to that of chemotherapy. That the primary product of iNOS is mycobacteriacidal provides one type of evidence consistent with a role for iNOS in controlling *tuberculosis.* There are 4 more lines of evidence: (ii) immunologically activated, iNOS-expressing mouse macrophages can kill *M. tuberculosis,* but not if the macrophages are treated with iNOS inhibitors (Chan et al., "Killing of Virulent *Mycobacterium tuberculosis* by Reactive Nitrogen Intermediates Produced by Activated Murine Macrophages," *J. Exp. Med.* 175:1111-22 (1992)) or bear disrupted NOS2 alleles (Ehrt et al., "Reprogramming of the Macrophage Transcriptome in Response to Interferon-γ and *Mycobacterium tuberculosis*: Signaling roles of Nitric Oxide Synthase-2 and Phagocyte Oxidase," *J. Exp. Med.* 194: 1123-1140 (2001)); (iii) iNOS is expressed in infected mouse tissues in which the growth of Mtb is restrained, but iNOS is scant when immunosuppressive drugs or genetic interventions impair host resistance (reviewed in MacMicking et al., "Identification of Nitric Oxide Synthase as a Protective Locus Against *Tuberculosis,*" *Proc. Natl. Acad. Sci.* 94:5243-5248 (1997)); (iv) healthy mice that harbor tubercle *bacilli* succumb abruptly to TB following ingestion of specific iNOS inhibitors (MacMicking et al., "Identification of Nitric Oxide Synthase as a Protective Locus Against *Tuberculosis,*" *Proc. Natl. Acad. Sci.* 94:5243-5248 (1997); and Chan et al., "Effects of Nitric Oxide Synthase Inhibitors on Murine Infection with *Mycobacterium tuberculosis,*" *Infect. Immun.* 63:736-40 (1995)); and (v) mice with disrupted NOS2 alleles die with fulminant TB in a few weeks, while wild type mice survive infection for ~9 months (MacMicking et al., "Identification of Nitric Oxide Synthase as a Protective Locus Against *Tuberculosis,*" *Proc. Natl. Acad. Sci.* 94:5243-5248 (1997); Scanga et al., "The Inducible Nitric Oxide Synthase Locus Confers Protection Against Aerogenic Challenge of Both Clinical and Laboratory Strains of *Mycobacterium tuberculosis* in Mice," *Infect. Immun.* 69:7711-7717 (2001); and Mogues et al., "The Relative Importance of T Cell Subsets in Immunity and Immunopathology of Airborne *Mycobacterium tuberculosis* Infection in Mice," *J. Exp. Med.* 193:271-280 (2001)). When $O_2$ is limiting, Mtb uses nitrate as an electron acceptor, generating nitrite as a byproduct (Weber et al., "Anaerobic Nitrate Reductase (narGHJI) Activity of *Mycobacterium Bovis* BCG In vitro and its Contribution to Virulence in Immunodeficient Mice," *Mol. Micro.* 35:1017-1025 (2000)). This reaction is essential for mycobacterial proliferation in mouse lung, as judged by the failure of nitrate reductase-deficient BCG to proliferate even in immunodeficient mice (Weber et al., "Anaerobic nitrate Reductase (narGHJI) Activity of *Mycobacterium Bovis* BCG In vitro and its Contribution to Virulence in Immunodeficient Mice," *Mol. Micro.* 35:1017-1025 (2000)). Nitrate arises from dietary sources and the action of constitutively expressed NOSs, and is thus a normal component of human blood and bronchoalveolar fluid. Nitrite regenerates NO at the mildly acidic pH pertaining in poorly oxygenated microenvironments (Stuehr et al., "Nitric Oxide: A Macrophage Product Responsible for Cytostasis and Respiratory Inhibition in Tumor target Cells," *J. Exp. Med.* 169:1543-5 (1989)). Thus, Mtb needs to survive nitrosative stress generated by itself as well as by the host.

The existing armamentarium against Mtb is clinically effective when the organism is drug-sensitive and 180-270 days of drug administration are ensured by directly observed therapy. Both conditions are hard to meet. Agents are urgently needed that target additional pathways. Most approaches to antibiotic development are based on screening for compounds that inhibit the growth of the organism in pure culture, or testing inhibitors of pathways already known to be essential for growth in pure culture. Rarely has an effort been made to screen under conditions that model a critical aspect of the host-pathogen relationship. For Mtb, intraphagosomal conditions include low $Fe^{2+}$, low $Mg^{2+}$, and increased oxidative/nitrosative stress (Buchmeier et al., "A Parallel Intraphagosomal Survival Strategy Shared by *Mycobacterium Tuberculosis* and Salmonella enterica," *Molec. Microbiol.* 35:1375-82 (2000); Forbes et al., "Divalent-Metal Transport by NRAMP Proteins at the Interface of Host-Pathogen Interactions," *Trends Microbiol.* 9:397-403 (2001); and Nathan et al., "Reactive Oxygen and Nitrogen Intermediates in the Relationship Between Mammalian Hosts and Microbial Pathogens," *Proc. Natl. Acad. Sci. USA* 97:8841-8848 (2000)). The clinical immunobiology of Mtb infection teaches that chemotherapy that is effective in vitro is less effective in the host whose immune system does not contribute to control. In the mouse, chemotherapy that works in vitro is only transiently effective in a host that lacks iNOS.

Thus, TB is the leading cause of death from a single bacterial infection and the leading opportunistic infection in HIV-infected hosts. Multiple drug resistance is rapidly spreading and exacerbates these burdens, and the threat of bioterrorism adds a new dimension to the picture. New chemotherapeutic options are needed that work faster and on additional targets than those now available. In particular, it would be useful to have more information about the genes that allow Mtb to resist host antibacterial mechanisms for the development of anti-infectives in the treatment of Mtb infection.

The present invention is directed to overcoming these and other deficiencies in the art.

SUMMARY OF THE INVENTION

The present invention relates to a method of treating pathogen infection in a subject. This method involves inhibiting proteasomal activity in a pathogen under conditions effective to make the pathogen susceptible to antibacterial host defenses, thereby treating the pathogen infection in the subject.

The present invention also relates to another method of treating pathogen infection in a subject. This method involves inhibiting enzyme activity in a pathogen under conditions effective to make the pathogen susceptible to antibacterial host defenses. The enzyme in this method is selected from the group consisting of a DNA repair enzyme and a flavin-like co-factor synthesis enzyme.

The present invention also relates to another method of treating pathogen infection in a subject. This method involves inhibiting proteasomal activity in a pathogen under conditions effective to make the pathogen susceptible to antibacterial host defenses and inhibiting enzyme activity in a pathogen under conditions effective to make the pathogen susceptible to antibacterial host defenses. As a result, pathogen infection in the subject is treated.

The present invention relates to a method of screening a known or suspected proteasomal inhibitor compound for an ability to sensitize bacteria to antibacterial effects of oxidative/nitrosative stress. This involves growing bacteria in a medium containing an exogenous stress-inducing agent under conditions effective to induce oxidative/nitrosative stress in the bacteria, adding a known or suspected proteasomal inhibitor compound to the medium, and determining whether the bacteria survive or fail to survive. The failure to survive indicates an ability of the inhibitor compound to sensitize the bacteria to antibacterial effects of oxidative/nitrosative stress.

Another aspect of the present invention is a method of screening a known or suspected DNA repair enzyme inhibitor compound for an ability to sensitize bacteria to antibacterial effects of oxidative/nitrosative stress. This involves growing bacteria in a medium containing an exogenous stress-inducing agent under conditions to induce oxidative/nitrosative stress in the bacteria, adding a known or suspected DNA repair enzyme inhibitor compound to the medium, and determining whether the bacteria survive or fail to survive. The failure to survive indicates an ability of the inhibitor compound to sensitize bacteria to antibacterial effects of oxidative/nitrosative stress.

The present invention also relates to method of screening a known or suspected flavin-like co-factor synthesis enzyme inhibitor compound for an ability to sensitize bacteria to antibacterial effects of oxidative/nitrosative stress. This involves growing bacteria in a medium containing an exogenous stress-inducing agent under conditions effective to induce oxidative/nitrosative stress in the bacteria, adding a known or suspected flavin-like co-factor synthesis enzyme inhibitor compound to the medium, and determining whether the bacteria survive or fail to survive. The failure to survive indicates an ability of the inhibitor compound to sensitize bacteria to antibacterial effects of oxidative/nitrosative stress.

Another aspect of the present invention is a method of screening a proteasomal inhibitor test compound for an ability to sensitize bacteria to the antibacterial effects of oxidative/nitrosative stress. This method involves providing an isolated protein having proteasomal activity, a reagent upon which the isolated protein exerts activity; and a proteasomal inhibitor test compound. The protein, the reagent, and the test compound are blended to form a mixture. The activity of the protein upon the reagent in the mixture is determined. Any difference between the activity of the protein upon the reagent with and without the test compound is measured, thereby screening the test compound for an ability to sensitize bacteria to the antibacterial effects of oxidative/nitrosative stress.

The infectious persistence and multiple drug resistance of M. tuberculosis (MDR-Mtb) are a bioterrorism threat and a global challenge to health. Yet little new chemotherapy against Mtb has emerged in decades. A fresh approach to anti-infective chemotherapy for Mtb is to target a pathway in the pathogen that while dispensable or not strictly essential in vitro, is essential for the pathogen to survive in the host. Such a target is the resistance of Mtb to the oxidative and nitrosative stress imposed by macrophages.

BRIEF DESCRIPTION OF THE DRAWINGS

FIG. 1 is an example of the screening method for mutants. Shown are OD (optical density) readings for a microtiter plate with 60 mutants after incubation in 1.5 mM nitrite at pH 5.5 for 3 days, subculture into medium at pH 6.6, and outgrowth for 16 days. Mutant in well G4 contains an insertion in Rv2115c.

FIG. 2A shows the survival of wild-type ("wt") Mtb H37Rv and 12 mutants after 6 days exposure to pH 5.5 with or without 3 mM $NaNO_2$. Treated cultures were diluted 1:4 in nitrite-free medium near neutrality (pH 6.6) and the OD was monitored 21 days later. OD immediately after the 1:4 dilution was barely detectable. FIG. 2B shows the ability of the mutants to survive nitrite. Treated bacteria were plated on agar and colony forming units ("CFU") counted 14-20 days later. Open bars signify CFU at the beginning of the 6-day treatment. Means+SD of triplicates. Genes are designated below the columns. Numbers in parentheses indicate the codon in which the transposon inserted.

FIG. 3 is an alignment of genomic regions encoding proteasome components in Mtb (Mt) and two other Actinomycetes, *Streptomyces coelicolor* (Sc) and *Rhodococcus erythropolis* (Re). FIG. 2 is modeled on one in (Nagy et al., "The 20S Proteasome of *Streptomyces Coelicolor*," *J. Bacteriol.* 180(20):5448-5453 (1998), which is hereby incorporated by reference in its entirety). Proteasome-associated genes are represented in black. Homologs are joined by dashed lines. Percent identities are circled. Genes identified in the screen are shown as outlined arrows.

FIGS. 4A-B characterize proteasome-associated genes and their mutants. FIG. 4A shows the self-association of Rv2115c and mutual association of PrcB and PrcA. *E. coli* lacking endogenous adenylate cyclase were transformed with two plasmids encoding either of two domains of *Bordetella pertussis* cyclase, T18 or T25, in fusion with Rv2115c (R), PrcA (A), PrcB (B) or no other protein (empty vector, E). Protein-protein interactions that reconstituted functional cyclase allowed cAMP-dependent expression of β-galactosidase (Karimova et al., "A Bacterial Two-Hybrid System Based on a Reconstituted Signal Transduction Pathway," *Proc. Natl. Acad. Sci. USA* 95(10):5752-5756 (1998), which is hereby incorporated by reference in its entirety). Means+SD for two experiments, each in duplicate. FIG. 4B shows the growth rates of the proteasome-associated mutants (dashed lines) and wt Mtb (solid line) in 7H9-ADNaCl medium. Means+SD for 3 cultures of each strain.

FIGS. 5A-D show the single-copy complementation of an Rv2115c mutant with a transposon insertion at codon 77 (Rv2115c-77). Mutant and wt strains were transformed with vector alone (pMV306) or with the wt allele of Rv2115c (pMV-mpa). FIG. 5A show survival of mutants. Bacteria were exposed to 3 mM nitrite pH 5.5 for 7 days, then plated on agar to determine CFU. Means+SD of triplicates. FIG. 5B shows the susceptibility of the mutants to heat (45° C., 24 h). FIG. 5C shows the susceptibility of the mutants to isoniazid (0.06 μg/ml, 24 h). FIG. 5D shows the susceptibility of the mutants to $H_2O_2$ (5 mM, 4 h) compared among wt Mtb H37Rv and Rv2115c (with or without complementation), Rv2097c and uvrB mutants. Surviving bacteria were plated to determine CFU. Bacteria in FIG. 5B(b), FIG. 5C(b), and FIG. 5D(b) were plasmid-transformed.

FIG. 6A shows the failure of Rv2115c- and Rv2097c-mutant Mtb to grow in wt macrophages. FIG. 6B shows the failure of Rv2115c- and Rv2097c-mutant Mtb to grow in iNOS−/− macrophages. Bone marrow-derived macrophages from C57BL/6 wt (FIG. 5A) and iNOS−/− (FIG. 6B) mice were infected with Mtb H37Rv, Rv2115c-77 or Rv2097c-282. At times shown, monolayers were washed, macrophages lysed, and bacteria plated for CFU. Means of triplicates+SD from one of 3 similar experiments.

FIGS. 7A-B shows H37Rv infected wt and iNOS−/− lungs. FIGS. 7C-D shows Rv2115c infected wt and iNOS−/− lungs.

FIGS. 9A-B shows H37Rv infected wt and iNOS−/− lungs.

FIGS. 10A-B shows the recovery in the lungs, FIGS. 10C-D in the spleens, and FIGS. 10E-F in the livers of mice at days 1 (n=3), 21 (n=4) and 56 (n=3-4) after aerosol infection and upon euthanasia of moribund iNOS−/− mice (asterisk) on day 61 (n=5) (means+SD). FIGS. 10B, D, and F show the effect of complementing the Rv2115-mutant Mtb by inserting a wt copy of the Rv2115c gene into the chromosome at the integrative attB site. The same plasmid without Rv2115c was also inserted into wt Mtb and the Rv2115c mutant.

FIG. 11A: MLN-273, but not its enantiomer MLN-293, inhibited proteasomal protease activity in Mtb lysates against a tetrapeptide substrate. FIGS. 11B-D: MLN-273, but neither MLN-293 nor vehicle (DMSO), inhibited growth of wt Mtb and Rv2115c and Rv2097c mutants under standard culture conditions. MLN-273, MLN-293 (50 µM each) or DMSO (2% vol/vol) were added on day 0.

FIG. 13A shows outgrowth 6 days after subculture of Mtb that had previously been incubated in medium at pH 5.5 without nitrite. FIG. 13B shows outgrowth 15 days after subculture of Mtb that had previously been incubated in medium at pH 5.5 with nitrite. Following the exposure to nitrite, a longer period of outgrowth of surviving bacteria was necessary before absorbance became detectable.

FIG. 14A: epoxomicin (epoxo, 50 µM), an irreversible proteasome inhibitor, but not MLN-273 (273) (100 µM), a reversible inhibitor, augmented the anti-mycobacterial effect of nitrite when the inhibitors and nitrite were removed simultaneously by plating bacteria on agar after 6 days of exposure. In FIG. 14B-C, both proteasome inhibitors augmented the anti-mycobacterial effect of nitrite if present after nitrite-mediated injury. FIG. 14B: epoxomicin and MLN-273, but not MLN-293, enhanced the anti-mycobacterial effect both when added along with nitrite at day 0, and when added only after the subculture on day 6, plating on day 10, shown in FIG. 14C. FIG. 14D: MLN-273 (25 µM), added on day 6 as in FIG. 14C, augmented nitrite-mediated injury of both wt and Rv2115c-mutant Mtb. Means+SD for triplicates in 1 of 2 similar experiments.

DETAILED DESCRIPTION OF THE INVENTION

Figure 2:
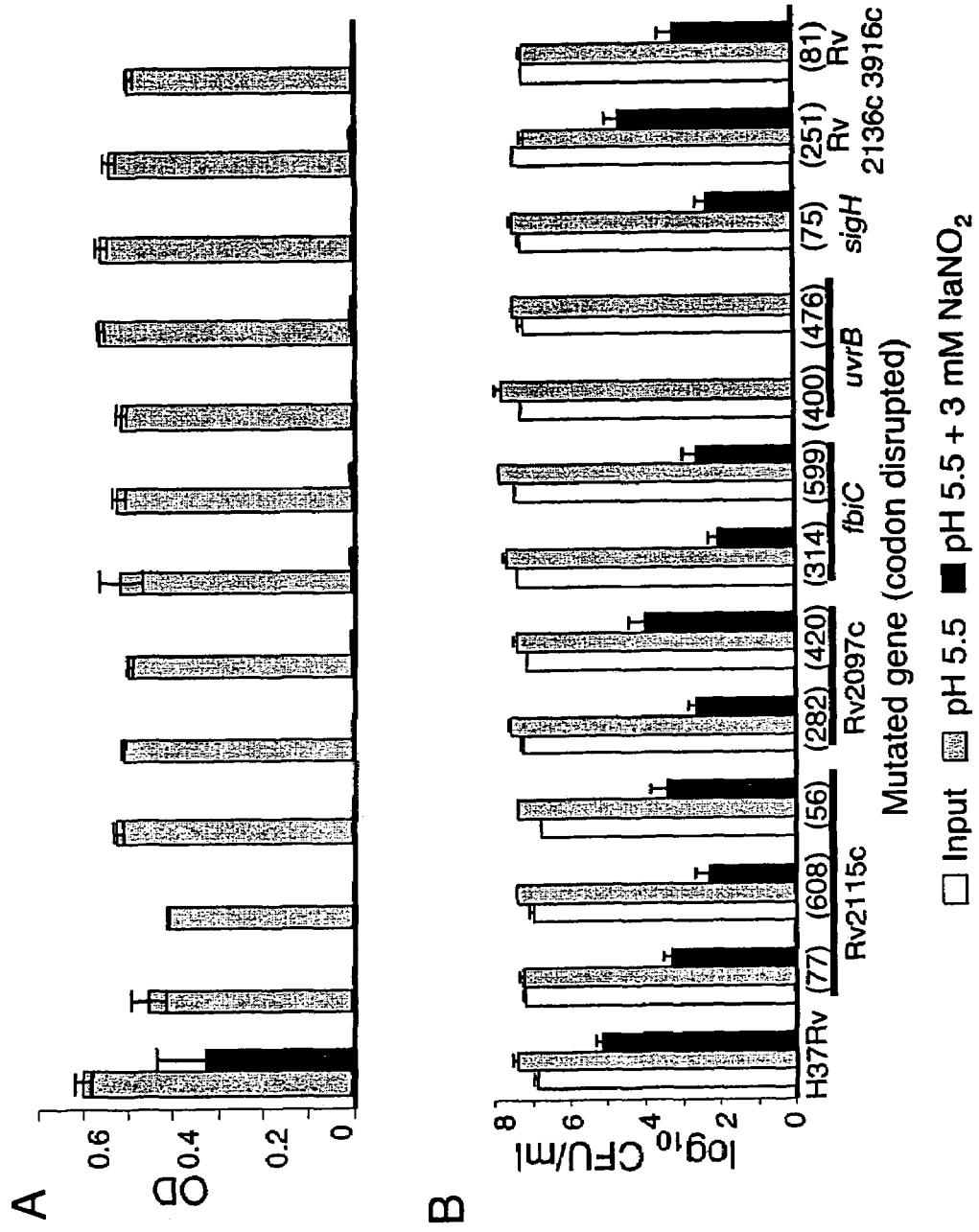
FIGS. 2A-B quantify the phenotype of RNI-sensitive mutants.
Figure 3:
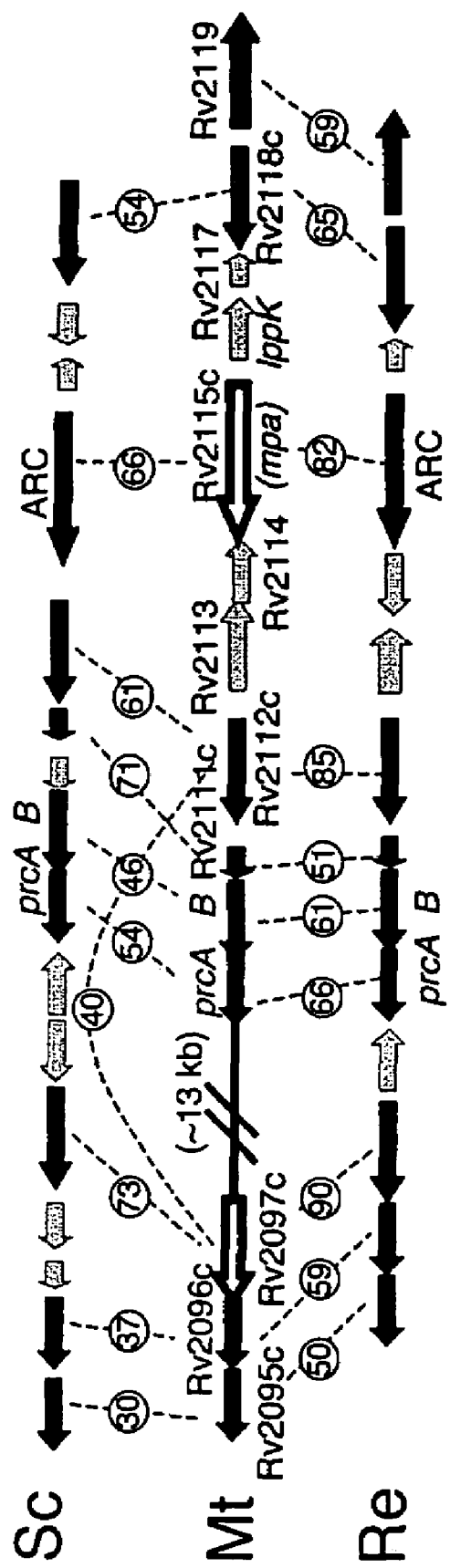

The present invention relates to a method of treating pathogen infection in a subject. This method involves inhibiting proteasomal activity in a pathogen under conditions effective to make the pathogen susceptible to antibacterial host defenses, thereby treating the pathogen infection in the subject.

In this aspect of the present invention, the proteosomal activity being inhibited is an AAA ATPase activity or a proteasomal protease activity. In one aspect of the present invention, the protease activity in a proteasome core is being inhibited. Suitable proteases for targeted inhibition in this aspect of the present invention include proteases that are products of the prcBA genes, including, but not limited to, PrcA and PrcB (Cole et al., "Deciphering the Biology of *Mycobacterium tuberculosis* From the Complete Genome Sequence," *Nature* 393:537-544 (1998); Nagy et al., "The 20S Proteasome of *Streptomyces coelicolor*," *J. Bacteriology* 180(20):5448-5453 (1998), which are hereby incorporated by reference in their entirety). In this aspect of the present invention, suitable AAA ATPases for inhibition include, without limitation, an AAA ATPase forming ring-shaped complex ("ARC"), a proteasome associated nucleotidase, a mycobacterial proteasome ATPase, and a proteasome accessory factor.

In this aspect of the present invention, suitable ARCs to be inhibited include, without limitation, products of the Rv2115c Mtb gene, products of the Rv2097c gene, and products of the GroEL1 gene.

The Rv2115c gene is predicted to encode an AAA ATPase forming ring-shaped complex (ARC) homologous to those found in proteasome caps in eukaryotes (Wolf et al., "Characterization of ARC, a Divergent Member of the AAA ATPase Family from Rhodococcus erythropolis," *J. Mol. Biol.* 277(1):13-25 (1998), which is hereby incorporated by reference in its entirety). Proteasomal deficiency can be achieved by disrupting the ARC AAA ATPase homolog (Rv2115c) (see Example 11, below).

Products of the GroEL1 gene suitable for being inhibited in this aspect of the present invention include, without limitation, the GroEL chaperone protein. The GroEL molecule, a ring-shaped complex, is an AAA ATPase of the same family as the proteasome-associated Rv2115c. The GroEL chaperonin is involved in promoting proper protein folding in bacteria (Walter S., "Structure and Function of the GroE Chaperone," *Cell. Mol. Life Sci.* 59:1589-1597 (2002), which is hereby incorporated in its entirety by reference). The bacterial protein cycle as a whole, from synthesis to degradation, relies on the GroEL chaperonin to fold nascent proteins as well as to repair denatured proteins (such as might arise from oxidative or nitrosative stress). It is the chaperonin's failures that are relegated to the proteasome (or its orthologs in eubacteria outside the Actinomycetes). Furthermore, inhibiting GroEL and the proteasome, in combination, is expected to be synergistic in killing Mtb, because it will hit two different locations in intersecting pathways providing alternate routes to the same vital cellular function.

In this aspect of the present invention, suitable inhibitors include, without limitation, N-[4-morpholine]carbonyl-β-[1-naphthyl]-L-alanine-L-leucine boronic acid (MLN-273) and epoxomicin (Kisselev et al., "Proteasome Inhibitors: from Research Tools to Drug Candidates," *Chem. Biol.* 8(8):739-758 (2001), which is hereby incorporated by reference in its entirety).

In this and all aspects of the present invention, "host defenses" is meant to include, without limitation, oxidative/nitrosative stress, including reactive nitrogen intermediate-induced stress ("RNI") and reactive oxygen intermediate-induced stress ("ROI").

In this aspect of the present invention, inhibiting is carried out by administering an inhibitor of proteasomal activity. The inhibitor can be administered by inhalation, orally, subcutaneously, intradermally, intraperitoneally, intravenously, intramuscularly, or by application to mucous membranes, such as, that of the nose, throat, and bronchial tubes.

The inhibitors of the present invention may be administered alone or with pharmaceutically or physiologically acceptable carriers, excipients, or stabilizers, and can be in solid or liquid form such as, tablets, capsules, powders, solutions, suspensions, or emulsions.

The solid unit dosage forms can be of the conventional type. The solid form can be a capsule, such as an ordinary gelatin type containing the desired inhibitor of the present invention and a carrier, for example, lubricants and inert fillers such as, lactose, sucrose, or cornstarch. In another embodiment, these compounds are tableted with conventional tablet bases such as lactose, sucrose, or cornstarch in combination with binders like acacia, cornstarch, or gelatin, disintegrating agents, such as cornstarch, potato starch, or alginic acid, and a lubricant, like stearic acid or magnesium stearate.

The inhibitors of proteosomal activity of the present invention may also be administered in injectable dosages by solution or suspension of the inhibitor in a physiologically acceptable diluent with a pharmaceutical carrier. Such carriers include sterile liquids, such as water and oils, with or without the addition of a surfactant and other pharmaceutically and physiologically acceptable carrier, including adjuvants, excipients or stabilizers. Illustrative oils are those of petroleum, animal, vegetable, or synthetic origin, for example, peanut oil, soybean oil, or mineral oil. In general, water, saline, aqueous dextrose and related sugar solution, and glycols, such as propylene glycol or polyethylene glycol, are preferred liquid carriers, particularly for injectable solutions.

For use as aerosols, the inhibitors of the present invention in solution or suspension may be packaged in a pressurized aerosol container together with suitable propellants, for example, hydrocarbon propellants like propane, butane, or isobutane with conventional adjuvants. The inhibitors of the present invention also may be administered in a non-pressurized form such as in a nebulizer or atomizer.

In this and all aspects of the present invention, suitable pathogens include, without limitation, *Mycobacterium tuberculosis, Mycobacterium leprae,* or another disease-causing *Mycobacterium*.

In this and all aspects of the present invention, suitable subjects are all mammals, including, without limitation, humans.

The present invention also relates to another method of treating pathogen infection in a subject. This method involves inhibiting enzyme activity in a pathogen under conditions effective to make the pathogen susceptible to antibacterial host defenses. Suitable enzymes targeted for inhibition in this aspect of the present invention include DNA repair enzymes and flavin-like co-factor synthesis enzymes.

In this aspect of the present invention, the DNA repair enzyme includes, without limitation, a nucleotide excision-repair (NER) enzyme (Theis et al., "The Nucleotide Excision Repair Protein UvrB, a Helicase-Like Enzyme with a Catch," *Mutat. Res.* 460(3-4):277-300 (2000), which is hereby incorporated by reference in its entirety). Suitable NER enzymes include, for example, those enzymes that are products of the uvr gene family, including, without limitation, UvrB (Theis et al., "The Nucleotide Excision Repair Protein UvrB, a Helicase-Like Enzyme with a Catch," *Mutat. Res.* 460(3-4):277-300 (2000), which is hereby incorporated by reference in its entirety).

In this aspect of the present invention, another suitable enzyme for inhibition is a flavin-like co-factor synthesis enzyme.

In this aspect of the present invention, host defenses, suitable pathogens, suitable subjects, and methods for administering inhibitors are all as described above.

The present invention also relates to another method of treating pathogen infection in a subject. This method involves inhibiting proteasomal activity in a pathogen under conditions effective to make the pathogen susceptible to antibacterial host defenses, and inhibiting enzyme activity in a pathogen under conditions effective to make the pathogen susceptible to antibacterial host defenses, thereby treating pathogen infection in the subject. In this aspect of the present invention, the proteosomal activity being inhibited is an AAA ATPase activity or a proteasomal protease activity, including those described above. In one aspect of the present invention, the protease activity in a proteasome core is being inhibited. Suitable proteases for targeted inhibition in this aspect of the present invention also include proteases that are products of the prcBA genes, including, but not limited to, PrcA and PrcB. In this aspect of the present invention, the AAA ATPase includes, without limitation, an AAA ATPase forming ring-shaped complex, a proteasome associated nucleotidase, a mycobacterial proteasome ATPase, and a proteasome accessory factor.

Suitable enzymes targeted for inhibition in this aspect of the present invention include DNA repair enzymes and flavin-like co-factor synthesis enzymes. DNA repair enzyme activity inhibited can be a nucleotide excision-repair enzyme (NER) activity. The NER enzyme includes, without limitation, those enzymes that are products of the uvr gene family, including, without limitation, UvrB. Another enzyme that is suitable in this aspect of the present invention is a flavin-like co-factor synthesis enzyme.

In this aspect, host defenses, suitable pathogens, suitable subjects, and methods for administering inhibitors are all as described above.

The present invention also relates to a method of screening a known or suspected proteasomal inhibitor compound for an ability to sensitize bacteria to antibacterial effects of oxidative/nitrosative stress. This involves growing bacteria in a medium containing an exogenous stress-inducing agent under conditions to induce oxidative/nitrosative stress in the bacteria, adding a known or suspected proteasome inhibitor compound to the medium, and determining whether the bacteria survive or fail to survive. The failure to survive indicates an ability of the inhibitor compound to sensitize bacteria to antibacterial effects of oxidative/nitrosative stress. "Survival" is determined using techniques such as those described in the Examples below, and others that are known and used in the art. An exemplary exogenous stress-inducing agent in this aspect of the present invention is nitrite.

In this aspect of the present invention, the proteosomal activity being inhibited is, for example, an AAA ATPase activity or a protease activity. In one aspect of the present invention, the protease activity of a proteasomal core is being inhibited. Suitable proteases for targeted inhibition in this aspect of the present invention include proteases that are products of the prcBA genes, including, but not limited to, PrcA and PrcB. In this aspect of the present invention, suitable AAA ATPases include, without limitation, an AAA ATPase forming ring-shaped complex, a proteasome associated nucleotidase, a mycobacterial proteasome ATPase, and a proteasome accessory factor.

In this and all aspects of the present invention involving screening of potential inhibitors, standard screening assays can be employed, such as those described in the Examples below. Generally, screening assays for inhibition of proteosomal activity in Mtb involve culturing cells infected with Mtb in a suitable growth medium, with or without an exogenous stress-inducing agent. A test compound is added to the culture medium thereby producing a "test culture." Typically, control runs are performed in which no test compounds are added to the culture. Failure of the treated Mtb to survive indicates inhibition of proteasomal activity. "Survival" is determined using techniques such as those described in the Examples below, and others that commonly used in the art (e.g., Kisselev et al., "Proteasome Inhibitors: from Research Tools to Drug Candidates," *Chem. Biol.* 8(8):739-758 (2001), which is hereby incorporated by reference in its entirety). Other assay methods may also be used to screen inhibitors of protease or enzyme activity, including in vitro screening assays. The present invention is not limited by the particular method of screening proteasomal inhibitors.

The present invention relates to a method of screening a known or suspected DNA repair enzyme inhibitor compound for an ability to sensitize bacteria to antibacterial effects of oxidative/nitrosative stress. This involves growing bacteria in a medium containing an exogenous stress-inducing agent under conditions to induce oxidative/nitrosative stress in the bacteria, adding a known or suspected DNA repair enzyme inhibitor compound to the medium, and determining whether the bacteria survive or fail to survive. The failure to survive indicates an ability of the inhibitor compound to sensitize bacteria to antibacterial effects of oxidative/nitrosative stress.

In this aspect of the present invention, a suitable DNA repair enzyme is any NER enzyme, including any that is products of the uvr gene family, including, without limitation, the excision-repair enzyme UvrB.

In this aspect of the present invention, oxidative/nitrosative stress, exemplary stress-inducing agents, suitable bacteria, and suitable methods for determination of survival are all as described above.

The present invention relates to a method of screening a known or suspected flavin-like co-factor synthesis enzyme inhibitor compound for an ability to sensitize bacteria to antibacterial effects of oxidative/nitrosative stress. This involves growing bacteria in a medium containing an exogenous stress-inducing agent under conditions to induce oxidative/nitrosative stress in the bacteria, adding a known or suspected flavin-like co-factor synthesis enzyme inhibitor compound to the medium, and determining whether the bacteria survive or fail to survive. The failure to survive indicates an ability of the inhibitor compound to sensitize bacteria to antibacterial effects of oxidative/nitrosative stress. In this aspect of the present invention, oxidative/nitrosative stress, exemplary stress-inducing agents, suitable bacteria, and suitable methods for determination of survival are all as described above.

Another aspect of the present invention is a method of screening a proteasomal inhibitor test compound for an ability to sensitize bacteria to the antibacterial effects of oxidative/nitrosative stress. This method involves providing an isolated protein having proteasomal activity, a reagent upon which the isolated protein exerts activity, and a proteasomal inhibitor test compound. The protein, the reagent, and the test compound are blended to form a mixture. The activity of the protein upon the reagent in the mixture is determined. Any difference between the activity of the protein upon the reagent with and without the test compound is measured, thereby screening the test compound for an ability to sensitize bacteria to the antibacterial effects of oxidative/nitrosative stress.

In this aspect of the present invention, the proteosomal activity being inhibited is, for example, an AAA ATPase activity or a protease activity. In one aspect of the present invention, the protease activity of a proteasomal core is being inhibited. Suitable proteases for targeted inhibition in this aspect of the present invention include proteases that are products of prcBA genes, including, but not limited to, PrcA, PrcB and protease 1.

Suitable AAA ATPases include, without limitation, an AAA ATPase forming ring-shaped complex, a proteasome associated nucleotidase, a mycobacterial proteasome ATPase, and a proteasome accessory factor.

Suitable AAA ATPases for inhibition include, without limitation, an AAA ATPase forming ring-shaped complex ("ARC"), a proteasome associated nucleotidase, a mycobacterial proteasome ATPase, and a proteasome accessory factor.

Suitable ARCs to be inhibited include, without limitation, proteins of the Rv2115c Mtb gene, the Rv2097c gene, and the GroEL1 gene.

Typically, the proteins or polypeptides of this aspect of the present invention are secreted into the growth medium of recombinant *E. coli,* and purified to about 95% homogeneity. To isolate the desired protein, the *E. coli* host cell carrying a recombinant plasmid is propagated, homogenized, and the homogenate is centrifuged to remove bacterial debris. The fraction containing the desired protein of the present invention is subjected to gel filtration in an appropriately sized dextran or polyacrylamide or affinity column to separate the proteins. Alternative methods may be used as suitable. Any methods of constructing expression vectors, and producing and purifying the recombinant proteins in this aspect of the present invention known in the art can be used in this aspect of the present invention, including those as described in Sambrook et al., *Molecular Cloning: A Laboratory Manual,* Third Edition, Cold Spring Harbor: Cold Spring Harbor Laboratory Press, New York (2001) (which is hereby incorporated by reference in its entirety).

Also suitable in this aspect of the present invention are proteins that are modified by, for example, the deletion or addition of amino acids that have minimal influence on the properties, secondary structure, and hydropathic nature of the desired polypeptide. For example, a polypeptide or protein may be conjugated to a signal (or leader) sequence at the N-terminal end of the protein which co-translationally or post-translationally directs transfer of the protein. The polypeptide may also be conjugated to a linker or other sequence for ease of synthesis, purification, or identification of the polypeptide.

In this aspect of the present invention, the proteasomal proteins may be bacterial proteins of *Mycobacterium* spp., including, without limitation, *Mycobacterium tuberculosis*, *Mycobacterium leprae*, and another disease-causing *Mycobacterium*.

EXAMPLES

Example 1

Culturing *Mycobacterium tuberculosis*

Mtb was grown at 37° C. in Middlebrook 7H9 medium supplemented with 0.2% glycerol, 0.05% Tween-80, 0.5% bovine serum albumin, 0.2% dextrose, and 0.085% sodium chloride (7H9-ADNaCl). To test for sensitivity to nitrite in the high throughput screen, individual mutants were grown in 200 μl 7H9-ADNaCl in 96-well microtiter plates until growth was saturated. Aliquots (10-20 μl) of each culture were then subcultured into 200 pl of 7H9-ADNaCl that had been acidified to pH 5.5 with HCl and contained 1.5 mM $NaNO_2$. Trays were incubated at 37° C. After 3 days, 50 μl from each well was mixed with 150 μl 7H9-ADNaCl at pH 6.6. ODs were measured 14-21 days later in a plate spectrophotometer.

For CFU determinations, bacteria were plated on 7H 11-OADC agar and colonies enumerated 14-17 days later.

The two-hybrid experiments were performed as described (Karimova et al., "A Bacterial Two-Hybrid System Based on a Reconstituted Signal Transduction Pathway," *Proc. Natl. Acad. Sci. USA* 95:5752-6 (1998), which is hereby incorporated by reference in its entirety).

Example 2

Mouse Macrophage Infection

C57BL/6 mice were obtained from Jackson Laboratories (Bar Harbor, ME). Mice deficient in iNOS on the C57BL/6 background were from inventors' colony (Schaible et al., "Cytokine Activation Leads to Acidification and Increases Maturation of *Mycobacterium Avium*-Containing Phagosomes in Murine Macrophages," *J. Immunol.* 160(3):1290-1296 (1998), which is hereby incorporated by reference in its entirety) or purchased from Jackson Labs. For macrophage experiments, femoral bone marrow cells were seeded into 1 cm-diam wells at $1.5\times10^5$/well in 0.5 ml of Dulbecco's minimum Eagle's medium supplemented with 10% fetal bovine serum, 10 mM HEPES, 0.6 g/L L-glutamine, 1 mM pyruvate and 50 ng/ml recombinant mouse macrophage colony-stimulating factor (M-CSF) (R&D). After 7 days differentiation, the medium was replaced with fresh medium containing M-CSF at 10 ng/ml. Macrophages were infected with Mtb at a multiplicity of infection of 8. At indicated times, infected macrophages were washed and then lysed with 0.5% Triton X-100 to recover intracellular bacteria.

Mice were infected with wt Mtb or the Rv2115c-codon 77 mutant by aerosol to deliver ~200 *bacilli* per mouse, as determined by sacrificing 3 mice per strain of mouse and per strain of Mtb at day 1 and counting CFU recovered from the lungs.

Example 3

Proteasomal Protease Activity Assays

To measure proteasomal protease activity, Mtb was lysed by agitation with zirconia silica beads. The soluble fraction was filtered through a 0.45 micron filter. Aliquots of the filtrate (120 g protein) were incubated with succinyl-leu-leu-val-tyr-alpha-methylcoumarin (SEQ ID NO: 1) in the presence of 0.05% SDS and fluorescence was monitored. These conditions report activity of the mycobacterial proteasome (Knipfer et al., "Inactivation of the 20S Proteasome in *Mycobacterium smegmatis," Molec. Micro.* 25:375-83 (1997), which is hereby incorporated by reference in its entirety). The 50% inhibitory concentration was determined by applying the Hill equation to data from 2 experiments, each in triplicate. Epoxomicin was from Boston Biochem (Cambridge, Mass.).

For subculture after exposure of Mtb to proteasomal protease inhibitors, the initial cultures were diluted 1:4 in fresh, unacidified medium. Where test compounds were present before subculture, a sufficient amount more was added after subculture to restore the original concentrations.

Example 4

Preparation of Transposon Mtb Mutant Library and Identification of Nitrite Sensitive Mutants Using the mariner-based transposon MycoMarT7 (Sassetti et al., "Comprehensive Identification of Conditionally Essential Genes in Mycobacteria," Proc. *Natl. Acad. Sci. USA* 98:12712-7 (2001), which is hereby incorporated by reference in its entirety), a library was prepared consisting of approximately 10,100 kanamycin-resistant mutants of the H37Rv strain of Mtb. Mtb contains approximately 4,000 open reading frames (ORFs); thus, the library potentially has 1-2 hits per gene. Each mutant was exposed individually to 1.5 mM nitrite at pH 5.5 for three days, subcultured, and the OD generated by its growth 2-3 weeks later was recorded. Mutants were considered hypersensitive to nitrite if their cultures failed to reach an OD>0.05 absorbance units (AU) at a time when the OD of wild type (wt) Mtb cultures exceeded 0.3 AU, as shown in FIG. 1. Chromosomal DNA from colony-purified mutants was analyzed by Southern blot using the neo gene as a probe and transposon insertion sites were sequenced.

Fourteen mutants were hypersensitive to acidified nitrite. Each had a single, unique transposon insertion. Twelve of the mutants fell into five categories: DNA repair (uvrB), co-enzyme production (fbiC), transcriptional regulation (sigH), proteasome function (Rv2097c, Rv2115c), and unknown (Rv2136c and Rv3916c). The remaining two mutants, groEL1 and mbtF, grew poorly under standard conditions and not at all at pH 5.5. The mbtF mutant was set aside. The groEL1 mutant, which is more sensitive to low pH than it is to nitrite, may provide another avenue for Mtb killing.

Example 5

Characterization of Nucleotide Excision-Repair Mtb Mutants

The two mutants most susceptible to acidified nitrite contained transposon insertions in the nucleotide excision-repair (NER) gene uvrB. The NER system, consisting of UvrA, B, C and D, has been extensively studied in *E. coli* and is required for replacing nucleotides in DNA damaged by agents such as UV light (Theis et al., "The Nucleotide Excision Repair Protein UvrB, a Helicase-Like Enzyme with a Catch," *Mutat. Res.* 460(3-4):277-300 (2000), which is hereby incorporated by reference in its entirety). RNI, including products of iNOS, are mutagenic for viruses (Akaike, "Role of Free Radicals in Viral Pathogenesis and Mutation," *Rev. Med. Virol.* 11(2):87-101 (2001), which is hereby incorporated by reference in its entirety), bacteria (Zhuang et al., "Nitric Oxide-Induced Mutations in the HPRT Gene of hHuman Lymphoblastoid TK6 Cells and in *Salmonella typhimurium*," *Environ. Mol. Mutagen.* 35(1): 39-47 (2000), which is hereby incorporated by reference in its entirety), and mammalian cells (Zhuang et al., "Mutagenesis Associated with Nitric Oxide Production in Macrophages," *Proc. Natl. Acad. Sci. USA* 95(14):8286-91 (1998), which is hereby incorporated by reference in its entirety). *Salmonella typhimurium* uvrB mutants were more susceptible than wt bacteria to NO-dependent mutagenesis (Maragos et al., "Mutagenicity of Glyceryl Trinitrate (nitroglycerin) in *Salmonella typhimurium*," *Mutat. Res.* 298(3):187-95 (1993); Tamir et al., "DNA Damage by Nitric Oxide," *Chem. Res. Toxicol.* 9(5):821-7 (1996), which are hereby incorporated by reference in their entirety). Transcription of uvrA, uvrB, and uvrD1 was upregulated in Mtb-infected human macrophages (Graham et al., "Identification of *Mycobacterium tuberculosis* RNAs Synthesized in Response to Phagocytosis by Human Macrophages by Selective Capture of Transcribed Sequences (SCOTS)," *Proc. Natl. Acad. Sci. USA* 96(20):11554-11559 (1999), which is hereby incorporated by reference in its entirety). Because the two uvrB mutants were profoundly hypersusceptible to nitrite, it appears that RNI can damage DNA in Mtb and when this occurs, survival requires UvrB.

Example 6

Characterization of FbiC Mtb Mutants

Two mutants contained insertions in fbiC (Rv1173), a gene encoding a protein identical to FbiC (F420 biosynthesis) from *M. bovis* strain Bacille Calmette-Guérin (BCG) (Choi et al., "Demonstration That fbiC is Required by *Mycobacterium bovis* BCG for Co enzyme F(420) and FO Biosynthesis," *J. Bacteriol.* 184(9):2420-8 (2002), which is hereby incorporated by reference in its entirety). FbiC is required for the synthesis of a redox-active, flavin-like co-enzyme, F420. Several enzymes have been annotated in Mtb as F420-dependent (Cole et al., "Deciphering the Biology of *Mycobacterium tuberculosis* from the Complete Genome Sequence," *Nature* 393:537-44 (1998), which is hereby incorporated by reference in its entirety); however, none of the mutants identified in the screen had a disruption in a gene encoding such an enzyme. It is therefore possible that either FbiC itself or more than one F420-dependent enzyme is required for detoxification of RNI or repair of RNI-induced damage.

Example 7

Characterization of SigH Mtb Mutant

One mutant was disrupted in sigh, an alternative sigma factor that affects the expression of more than 100 genes in Mtb (Manganelli et al., "Role of the Extracytoplasmic-Function Sigma Factor Sigma(H) in *Mycobacterium tuberculosis* Global Gene Expression," *Mol. Microbiol.* 45(2): 365-74 (2002); Kaushal et al., "Reduced lnmunopathology and Mortality Despite Tissue Persistence in a *Mycobacterium tuberculosis* Mutant Lacking Alternative Sigma Factor, SigH," *Proc. Natl. Acad. Sci. USA* 99(12):8330-5 (2002), which are hereby incorporated by reference in their entirety). Disruption of sigH increased the sensitivity of Mtb in vitro to oxidants (Raman et al., "The Alternative Sigma Factor SigH Regulates Major Components of Oxidative and Heat Stress Responses in *Mycobacterium tuberculosis*," *J. Bacteriol.* 183(20):6119-25 (2001), which is hereby incorporated by reference in its entirety). The screening did not identify any genes in the proposed sigH regulon. If several sigH-dependent genes are required in combination for resistance to RNI, an insertion in any one of them would not result in RNI-susceptibility. A mutant with a targeted disruption in sigH grew in mice to similar numbers as wt Mtb, but caused less tissue pathology and mortality (Kaushal et al., "Reduced Immunopathology and Mortality Despite Tissue Persistence in a *Mycobacterium tuberculosis* Mutant Lacking Alternative Sigma Factor, SigH," *Proc. Natl. Acad. Sci. USA* 99(12):8330-5 (2002), which is hereby incorporated by reference in its entirety).

Example 8

Characterization of Proteasome-Associated Mtb Mutants

Organisms need intracellular proteases to process proproteins, inactivate regulatory proteins, and remove aberrant or irreversibly oxidized proteins. Compartmentalization helps restrict the action of proteases to proper substrates. Cytosolic protease comparttnentalization is achieved through a polymeric structure that confines active sites to the interior of a cylinder, access to which is regulated by ATPases of the "AAA" family ("AAA" ="ATPases associated with various activities") (Vale, R D. "AAA proteins: Lords of the Ring," *J. Cell Biol* 150:F13-19 (2000); Langer, T. "AAA Proteases: Cellular Machines for Degrading Membrane Proteins," *Trends in Biol. Sci.* 25:247-251 (2000); Ogura et al., "AAA Superfamily ATPases; Common Structure-Diverse Function. Genes to Cells," 6:575-97 (2001), which are hereby incorporated by reference in their entirety). In eukaryotes, the 20S proteasome is an approximately 700 kDa cylindrical structure composed of two rings of seven distinct subunits that sandwich two rings of seven distinct proteolytic β subunits. Proteasomes degrade short-lived regulatory proteins tagged by ubiquitin or related polypeptides. One function of the ubiquitin-proteasome pathway is in the selective removal of mutant, damaged, and misfolded proteins (Kisselev et al., "Proteasome Inhibitors: from Research Tools to Drug Candidates," *Chem. Biol.* 8(8):739-758 (2001), which is hereby incorporated by reference in its entirety). Archaeal 20S proteasomes and the presumptive proteasomes of eubacteria of the class Actinomycetes contain one type of a and one type of β subunit. In *R. erythropolis*, and *Streptomyces coelicolor*, the Rv2097c orthologs ORF9 (Karimova et al., "A Bacterial Two-Hybrid System Based on a Reconstituted Signal Transduction Pathway," *Proc. Natl. Acad. Sci. USA* 95:5752-6 (1998), which is hereby incorporated by reference in its entirety) and SCI41.23, respectively, are within one to two ORFs of prcBA. In *Mycobacterium leprae*, the Rv2097c ortholog, ML1328, is four ORFs downstream of prcBA (Cole et al., "Massive Gene Decay in the Leprosy Bacillus," *Science* 409(6823):1007-1011 (2001), which is hereby incorporated by reference in its entirety). In contrast, Rv2097c is separated from the prcBA locus by approximately 13 kb. However, Rv2097c lies immediately upstream of two genes, Rv2096c and Rv2095c, whose sequence and genetic organization are conserved in the proteasome-containing bacteria *M. leprae* (ML1329, ML1330), *S. coelicolor* (SCI41.20c, SCI41.19c), and *R. erythropolis* (ORF10(1), ORF11 (Karimova et al., "A Bacterial Two-Hybrid System Based on a Reconstituted Signal Transduction Pathway," *Proc. Natl.*

*Acad. Sci. USA* 95:5752-6 (1998), which is hereby incorporated by reference in its entirety). A homolog of Rv2097c, Rv2112c, is present on the Mtb chromosome two ORFs upstream of prcBA. Orthologs of Rv2112c are present in *M. leprae, R. erythropolis* and *S. coelicolor.*

Figure 4:
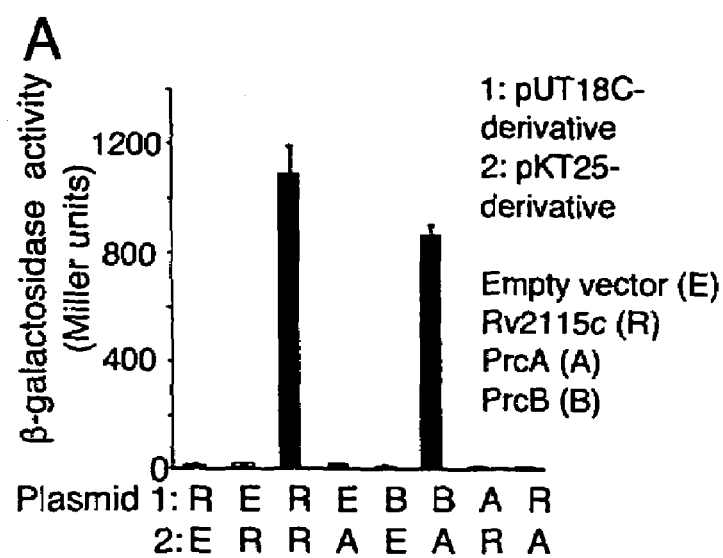
Figure 4:
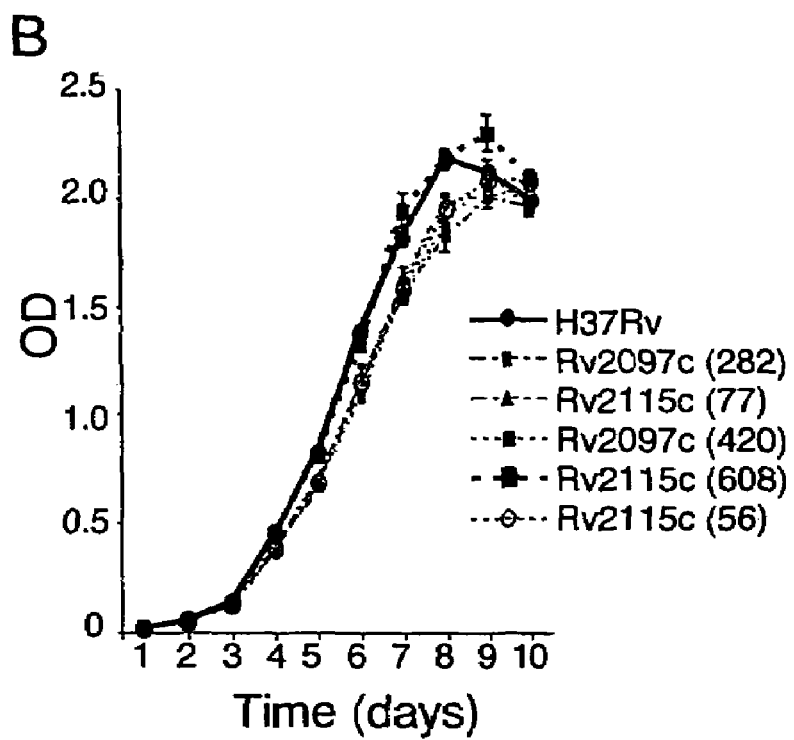

Proteomic analysis has demonstrated that Mtb makes Rv2115c, PrcA, and PrcB (Rosenkrands et al., "Towards the Proteome of *Mycobacterium tuberculosis,*" *Electrophoresis* 21(17):3740-3756 (2000), which is hereby incorporated by reference in its entirety). In studying mutual association of proteasomal subunits by the bacterial two-hybrid assay, no interactions were detected between Rv2115c and PrcA (AR and RA in FIG. 4A), nor between the pairs Rv2097c/PrcA and Rv2115c/Rv2097c, suggesting that other proteins (perhaps substrates) may be necessary for accessory proteins to interact with each other and the proteasomal core.

In studying the growth rates of the three Rv2115c and two Rv2097c mutants, it was noted that all but one of these 5 mutants had a subtle growth phenotype consisting in a delay of about 5 h beyond the 34 days that wt Mtb required to commence maximal growth. The exception was an Rv2115c mutant in which disruption in the penultimate codon (608) replaced a tyrosine codon with a stop codon. The minimally truncated protein evidently functions well enough under non-stressed conditions to allow the onset of rapid growth at the same time as wt Mtb. Nonetheless, the disrupted tyrosine may be critical for function during stress, as suggested by its conservation in proteasome-associated ATPases from archaea, bacteria, and eukaryotes.

Because the same phenotype of nitrite sensitivity arose in association with three mutations in Rv2115c and two in Rv2097c in a setting where each mutant strain contains only a single, unique transposon insertion, there is virtually no possibility that the phenotype arose from disruption of other loci. Moreover, Rv2115c appears to be monocistronic (Cole et al., "Deciphering the Biology of *Mycobacterium tuberculosis* from the Complete Genome Sequence," *Nature* 393:537-44 (1998), which is hereby incorporated by reference in its entirety); therefore, the transposon insertion is not likely to have polar effects. In contrast, Rv2097c is co-transcribed with Rv2096c and its disruption will exert polar effects on downstream gene(s). Complementation of the Rv2097c mutations awaits determination of the role of each gene in its operon.

Figure 8:
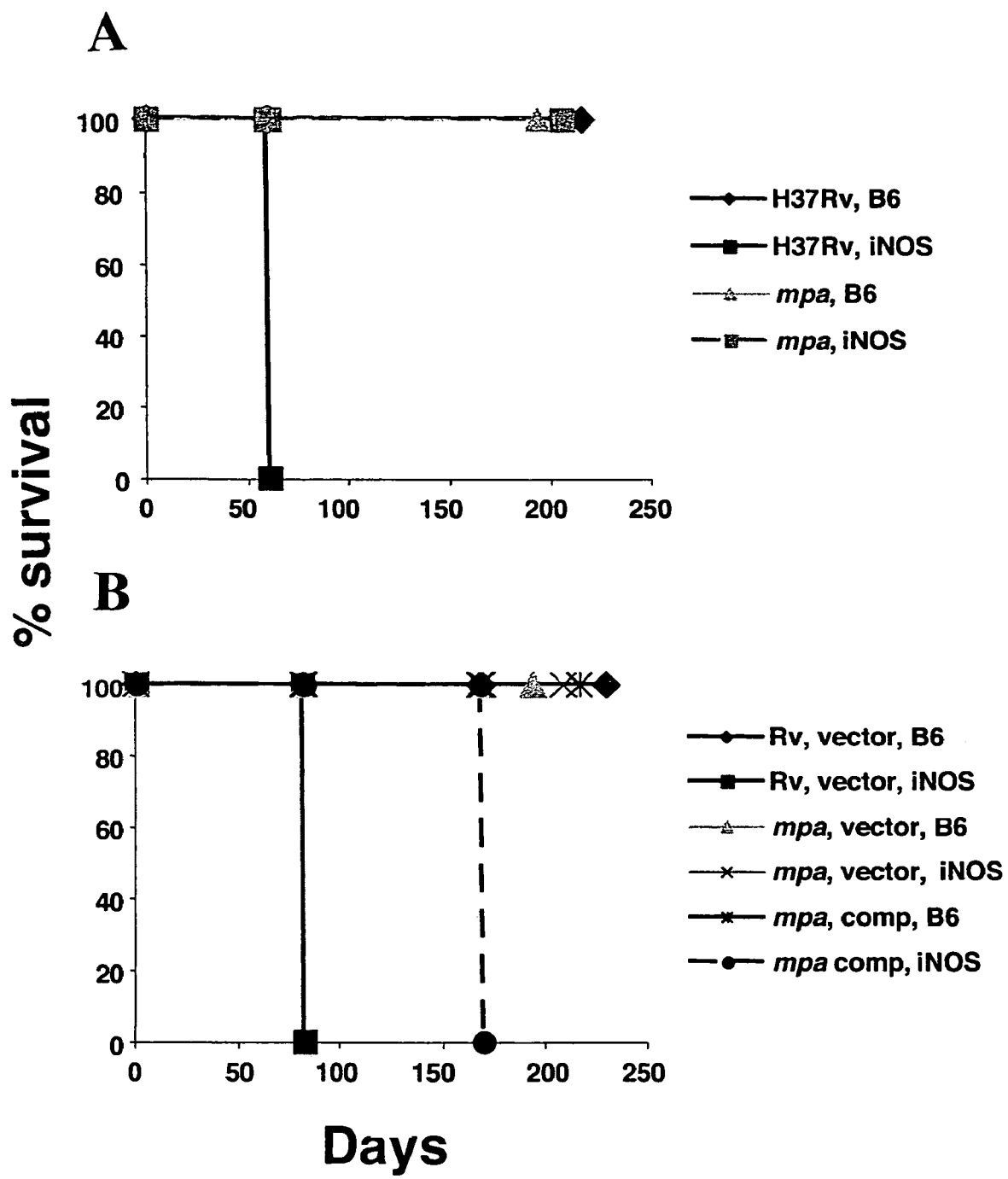
FIGS. 8A-B show the survival of wt and iNOS−/− C57BL/6 mice following aerosol infection with Mtb strains indicated. Mice were euthenized and scored as dead when moribund, as manifest by hunched posture, labored breathing, and markedly reduced movement. H37Rv: wt Mtb. mpa: H37Rv Mtb with Rv2115c gene disrupted by insertion of a transposon at codon 77. B6: wt C57BL/6 mice. iNOS: iNOS−/− mice on the C57BL/6 background.
Figure 9:
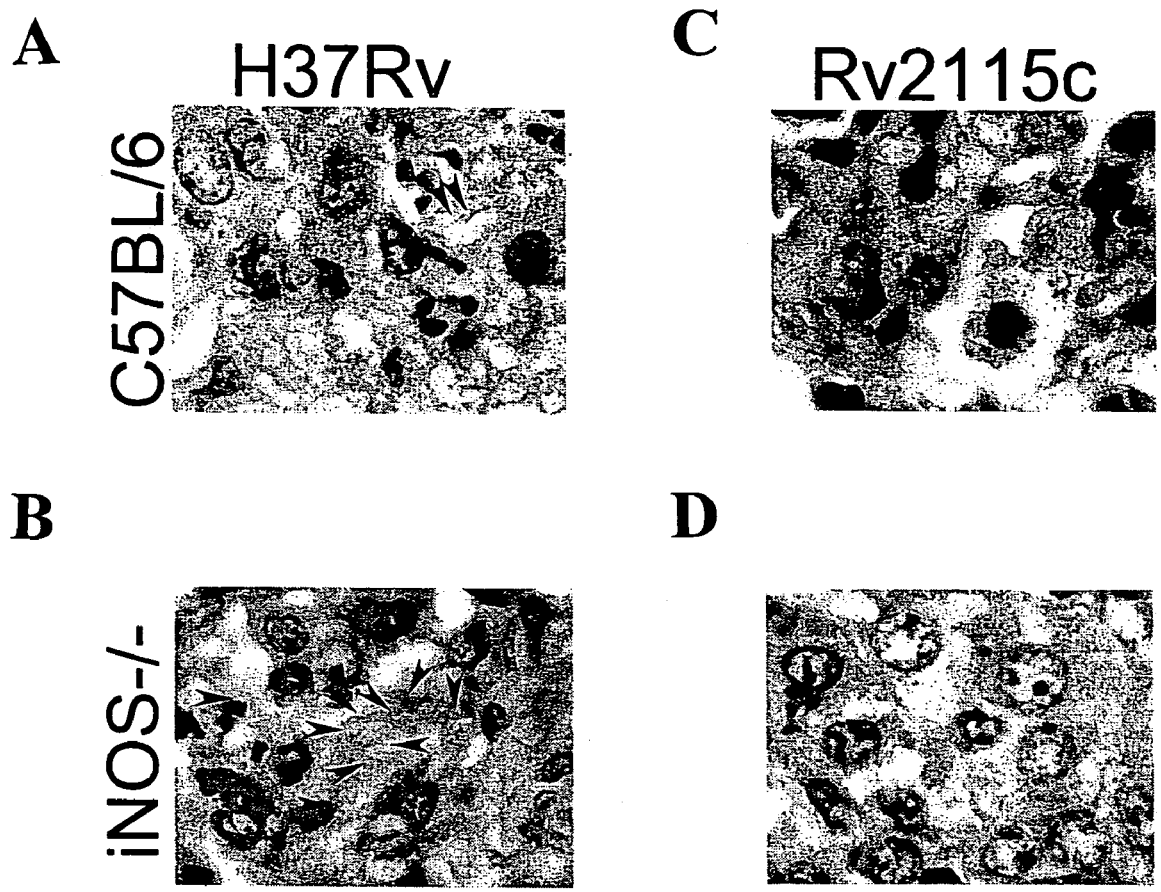
FIGS. 9A-B shows sections of the lungs shown in FIGS. 7E-H, stained by the Ziehl-Neelsen technique and photographed through a 100× objective.
FIGS. 9C-D shows Rv2115c infected wt and iNOS−/− lungs. Arrows indicate acid-fast bacteria. Only wt Mtb could be readily visualized.
Figure 10:
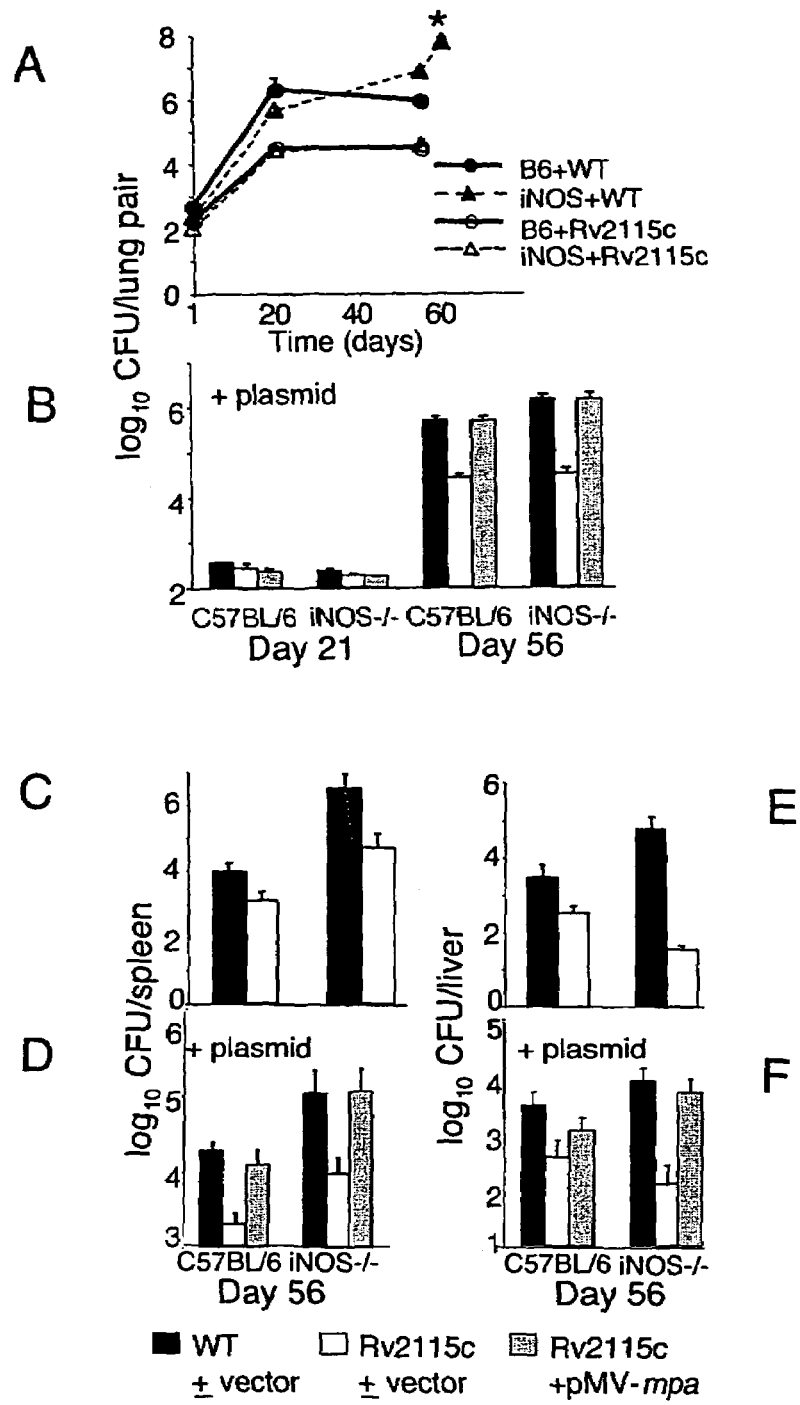
FIGS. 10A-F show the recovery of viable Mtb following infection.

Mouse infection experiments used Mtb both with and without plasmid transformation as a control for complementation of the Rv2115c mutation. By itself, the empty plasmid partially attenuated wt Mtb (time to death in iNOS−/− mice =83 days with plasmid vs. 61 days without plasmid). The complemented mutant killed iNOS−/− mice by 170 days; all other groups appeared well at 231 days (as shown in FIGS. 8A-B).

Not finding prcBA mutants in the screen led to the question of whether the transposon-mutant library contained prcBA mutants. They were sought by PCR and none could be detected. Likewise, Sassetti et al. concluded that mutants in the prcBA operon were either under-represented or absent in a 100,000-mutant transposon library grown under standard culture conditions (Sassetti et al., "Genes Required for Mycobacterial Growth Defined by High Density Mutagenesis," *Mol. Microbiol.* 48(1):77-84 (2003), which is hereby incorporated by reference in its entirety).

Other genes that contribute to RNI resistance could have been missed in this screen, because the library was not saturating; because the mutants died or grew too slowly to be represented in the library (for example, mutations in prcBA and the sucB and lpd components of the peroxynitrite reductase) (Sassetti et al., "Genes Required for Mycobacterial Growth Defined by High Density Mutagenesis," *Mol. Microbiol.* 48(1):77-84 (2003); Bryk et al., "Metabolic Enzymes of *Mycobacteria* Linked to Antioxidant Defense by a Thioredoxin-Like Protein," *Science* 295(5557):1073-1077 (2002), which are hereby incorporated by reference in their entirety); because the genes were not expressed under the conditions studied; or because the gene products afford redundant protection against nitrite or are active against other RNI. The function of the proteasome in protection against oxidative or nitrosative stress may be indirect, for example, if the proteasome degrades a repressor of an antioxidant defense.

Example 9

High-throughput Screening of Chemical Libraries Against Mtb Rv2115c ATPase

Large-scale, high through-put screening of chemical libraries that contain potential compounds capable of inhibiting bacterial proteasomal protease activity is an important step in identifying inhibitors to be ultimately tested in Mtb survival and growth assays, as described herein above. An exemplary high-throughput screening of a chemical library for an inhibitor of an Mtb Rv2115c gene product is carried out generally as follows.

An overexpression vector is constructed or Mtb Rv2115c in *E. coli* using a hexahistidine fusion to the amino-terminus or carboxyl-terminus of the protein. The protein is purified to >95% homogeneity from lysates of recombinant *E. coli*. The pH optimum is determined (7.4) and the $Mg^{2+}$ ion dependence is determined (10 mM). The basis of the assay is to use luciferase and luciferin to determine the remaining ATP concentration after incubating ATP with Rv2115c protein alone or following pre-incubation of Rv2115c protein with library test compounds for a predetermined amount of time at 37° C.

Specifically, the assay can be performed in a 384-well plate as follows. One μL of library compound in DMSO is added to each well. One μl of protein of predetermined optimized concentration is added, followed by 2 μl of 5×reaction buffer (250 mM Tris-HCl, 50 mM $MgCl_2$, 500 mM NaCl, pH 7.4). Water is added to bring the volume up 8 μl total. The plate is mixed and incubated at an appropriate temperature for the optimized amount of time. Two μl of ATP at optimized concentration is added. The plate is mixed and incubated at 37° C. for the optimized amount of time. Ten μl of Kinase-Glo™ reagent (Promega, Madison, Wis.), or a similar product, is added to all wells, and the plate is mixed and incubate for 10 minutes at room temperature. Luminescence is detected using a plate-reading luminometer.

Example 10

High-throughput Screening of Chemical Libraries Against Mtb Proteasomal ProteaseI An exemplary high-throughput screening of a chemical library for an inhibitor of the Mtb gene product proteaseI is carried out generally as follows.

An overexpression vector is constructed for Mtb prcBA genes in *E. coli* using pEt-30b(+) vector and a hexahistidine fusion to the carboxyl-terminus of the prcB gene. The protein is purified to >95% homogeneity from lysates of recombinant *E. coli* by an affinity column (Ni-NTA agarose) purification. Kinetic characterization is-performed for chymotrypsin-like activity, the impact of varying concentrations of SDS (0.05%) and the pH-rate profile (pH 8.0). The assay uses Suc-Leu-Leu-Val-Tyr-alpha-methyl coumarin (SEQ ID NO: 1) (AMC) as a proteasome substrate to measure the remaining activity of the proteasomal protease after pre-incubation with library compounds for the optimized amount of time at 37° C.

Specifically, the assay can be performed in a 384-well plate as follows. One μl of library compound in DMSO is added to each well. Five μl of 10× reaction buffer (0.5M Tris-HCl, 50 mM $MgCl_2$, pH 8.0), and five μl of protein of optimized concentration are added. Five μl 10×SDS of optimized concentration is added. Water is added to make up total 46 μl. The plate is mixed and incubated for optimized amount of time. Five μl of 10× substrate of optimized concentration is added. The plate is mixed and incubated at 37° C. for the optimized amount of time. Fifty μl of 10% SDS in $H_2O$ is added to stop the reaction. Mix the plate and incubate for 2 minutes at room temperature. Fluorescence is determined using a plate-reading microfluorimeter at excitation 370 nm, emission 430 nm.

Example 11

Identification of Mtb Genes Required for RNI Resistance

Figure 5:
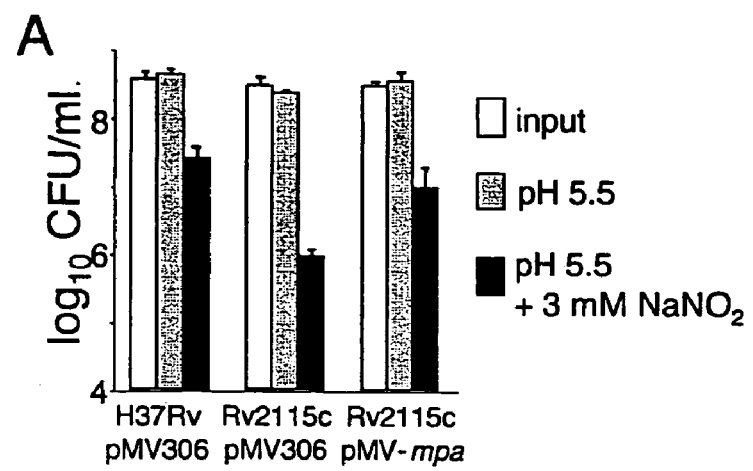
FIGS. 5B-D Means+SD (6 replicates, 2 experiments).
Figure 5:
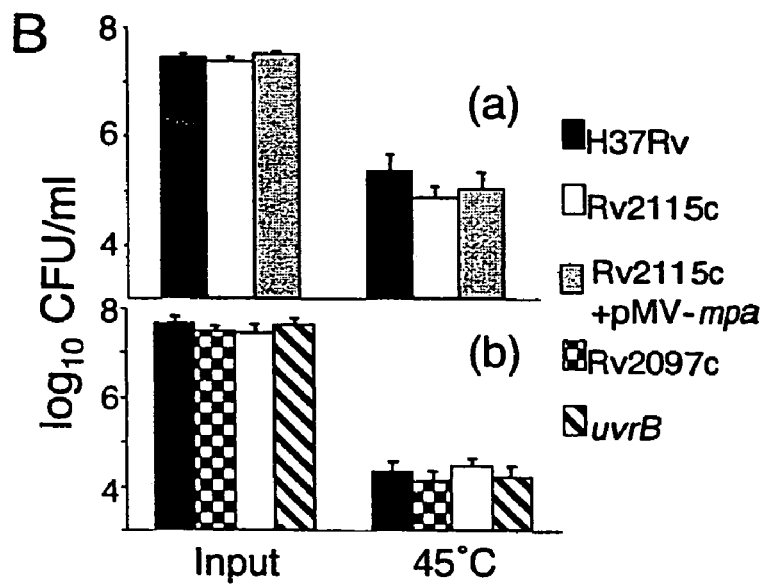
Figure 5:
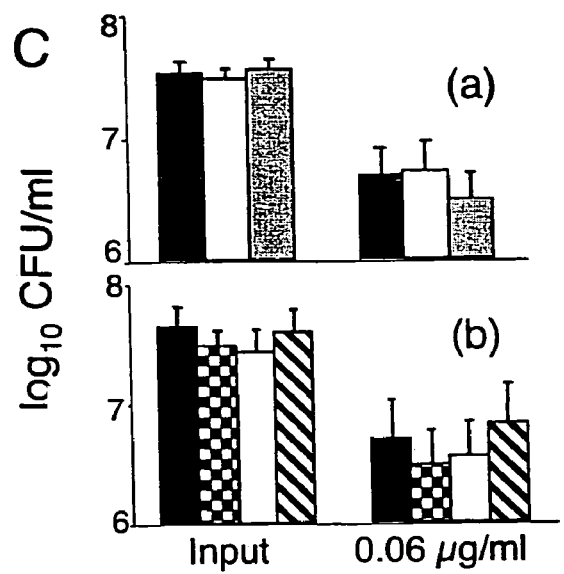
Figure 5:
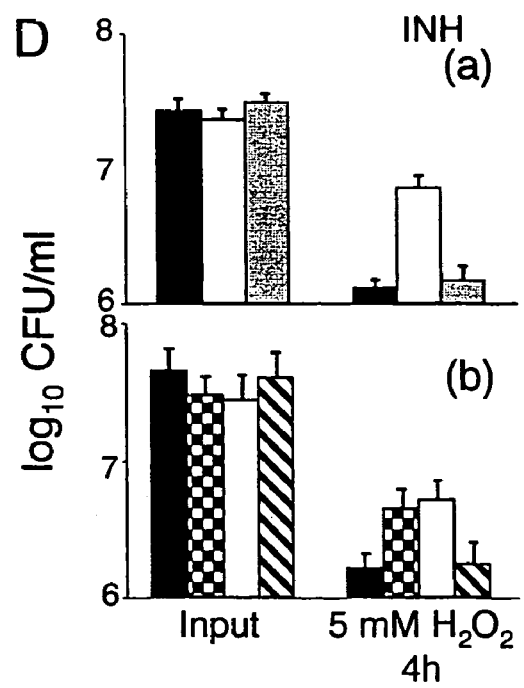

To identify Mtb genes required for resistance against RNI, approximately 10,100 transposon mutants were screened individually for increased sensitivity to nitrite at pH 5.5. Twelve mutants were hypersensitive. To quantify their phenotype, bacteria were exposed to pH 5.5 with or without 3 mM $NaNO_2$ for 6-7 days and then monitored in two ways. First, to assess both growth inhibition and killing, as shown in FIGS. 2A-B, cultures were diluted 1:4 in unacidified medium (pH 6.6). The final pH (6.5) decreased the generation of NO from residual nitrite. At this point, the OD of the cultures was barely detectable. Increased OD resulting from bacterial growth was recorded 2-3 weeks later. In control cultures with no nitrite, the 12 mutants grew as well as the wt strain after exposure to pH 5.5. In contrast, after exposure to nitrite, the mutants barely grew at all, as shown in FIG. 2A. Second, to assess killing, the bacteria were plated on agar and CFU counted after 2-3 weeks, shown in FIG. 2B. The degree to which individual mutants survived nitrite ranged from almost nil to the same as wt, shown in FIG. 2A.

Five of the 12 mutants had insertions in two genes encoding putative components of the proteasome. Proteasomes, which are essential in eukaryotes (Kisselev et al., "Proteasome Inhibitors: from Research Tools to Drug Candidates," *Chem. Biol*. 8(8):739-758 (2001), which is hereby incorporated by reference in its entirety), are responsible for degrading proteins that have been irreversibly oxidized (Davies, "Degradation of Oxidized Proteins by the 20S Proteasome," *Biochimie*. 83(3-4):301-10 (2001), which is hereby incorporated by reference in its entirety), such as by peroxynitrite (Grune et al., "Peroxynitrite Increases the Degradation of Aconitase and Other Cellular Proteins by Proteasome," *J. Biol. Chem*. 273(18):10857-10862 (1998), which is hereby incorporated by reference in its entirety). The eukaryotic 26S proteasome is composed of a 20S (700 kDa) core capped by one or two 19S regulatory structures. The base of the cap is a ring of six ATPases of the AAA class (ATPase associated with various activities) that participate in unfolding substrates, while the lid of the cap contains proteins required for substrate recognition, binding, and deubiquitinylation (Kisselev et al., "Proteasome Inhibitors: from Research Tools to Drug Candidates," *Chem. Biol*. 8(8):739-758 (2001), which is hereby incorporated by reference in its entirety). Much less is known about proteasomes in prokaryotes, where caps have not been identified and ubiquitin is exceptional (De Mot et al., "Proteasomes and Other Self-Compartmentalizing Proteases in Prokaryotes," *Trends Microbiol*. 7(2):88-92 (1999), which is hereby incorporated by reference in its entirety). The only eubacteria known to contain proteasomes are *Actinomycetes*. Mtb, an *Actinomycete,* is predicted to encode one type of a (from prcA) and one type of β subunit (from prcB), as shown in FIG. 3. Recombinant PrcA and PrcB from Mtb bound each other in a two-hybrid assay, shown in FIG. 4A, as expected for components of the proteasomal core. However, proteasomes have no known function in bacteria, where intracellular proteolysis is carried out by four other ATP-dependent, compartmentalized proteases of the ClpAP/XP, HslUV, FtsH, and Lon families. Mtb is unusual for a bacterium in lacking HslUV and Lon (Cole et al., "Deciphering the Biology of *Mycobacterium Tuberculosis* from the Complete Genome Sequence," *Nature* 393(6685):537-44 (1998), which is hereby incorporated by reference in its entirety).

Three of the Mtb proteasome-associated mutants had insertions in Rv2115c, a gene predicted to encode an AAA ATPase forming ring-shaped complex (ARC) homologous to those found in proteasome caps in eukaryotes, shown in FIG. 3 (Wolf et al., "Characterization of ARC, a Divergent Member of the AAA ATPase Family from *Rhodococcus erythropolis," J. Mol. Biol*. 277(1):13-25 (1998), which is hereby incorporated by reference in its entirety). Homologs of Rv2115c are known only in organisms with 20S proteasomes (FIG. 3). The Rv2115c homolog in *Rhodococcus erythropolis* (82% identity) forms hexameric or heptameric rings compatible with capping a 20S proteasome core (Wolf et al., "Characterization of ARC, a Divergent Member of the AAA ATPase Family from *Rhodococcus erythropolis," J. Mol. Biol*. 277(1):13-25 (1998), which is hereby incorporated by reference in its entirety). Another homologous ATPase ring structure, proteasome activating nucleotidase (PAN) from the archaeon *Methanococcus janaschii,* stimulated ATP-dependent unfolding and proteasomal degradation of proteins in vitro (Benaroudj et al., "PAN, the Proteasome-Activating Nucleotidase from Archaebacteria, is a Protein-Unfolding Molecular Chaperone," *Nat. Cell. Biol*. 2(11):833-839 (2000), which is hereby incorporated by reference in its entirety). Rv2115c conserves Walker A and B boxes and other motifs characteristic of proteasome-associated ATPases (Wolf et al., "Characterization of ARC, a Divergent Member of the AAA ATPase Family from *Rhodococcus erythropolis," J. Mol. Biol*. 277(1):13-25 (1998); and Benaroudj et al., "PAN, the Proteasome-Activating Nucleotidase from Archaebacteria, is a Protein-Unfolding Molecular Chaperone," *Nat. Cell. Biol*. 2(11):833-839 (2000), which are hereby incorporated by reference in their entirety). Two-hybrid analysis (Karimova et al., "A Bacterial Two-Hybrid System Based on a Reconstituted Signal Transduction Pathway," *Proc. Natl. Acad. Sci. USA* 95(10):5752-5756 (1998), which is hereby incorporated by reference in its entirety) demonstrated that Rv2115c monomers interact with each other, as expected for an ARC (FIG. 4A). Two mutants contained insertions in Rv2097c, a gene that is also annotated as a putative component of the proteasome (Cole et al., "Deciphering the Biology of *Mycobacterium Tuberculosis* from the Complete Genome Sequence," *Nature* 393(6685):537-44 (1998); and Nagy et al., "The 20S Proteasome of *Streptomyces Coelicolor," J. Bacteriol*. 180(20):5448-5453 (1998), which are hereby incorporated by reference in their entirety) based in part on its association with prcBA core genes, shown in FIG. 3. All three Rv2115c mutants and both Rv2097c mutants grew at the same maximal rates and to the same final culture density as wt Mtb under standard culture conditions, as shown in FIG. 4B.

Complementation with an integrative plasmid encoding wt Rv2115c restored to the Rv2115c-77 mutant the wt resistance to acidified nitrite, as shown in FIG. 5A. Notwithstanding its sensitivity to acidified nitrite, the Rv2115c mutant was just as susceptible as the wt and complemented strains to heat, as shown in FIG. 5B, and isoniazid, as shown in FIG. 5C. However, the Rv2115c mutant was more resistant to $H_2O_2$ than either wt Mtb or the complemented mutant, shown in FIG. 5D, perhaps reflecting compensatory induction of other anti-oxidant pathways. If Rv2097c participates in the same pathway as Rv2115c, it is likely that an Rv2097c mutant would have a similar signature of $H_2O_2$ resistance as the Rv2115c mutant. This proved to be the case, as shown in FIG. 5D. In contrast, a uvrB mutant was no more or less susceptible to $H_2O_2$ than wt Mtb, as shown in FIG. 5D.

Figure 6:
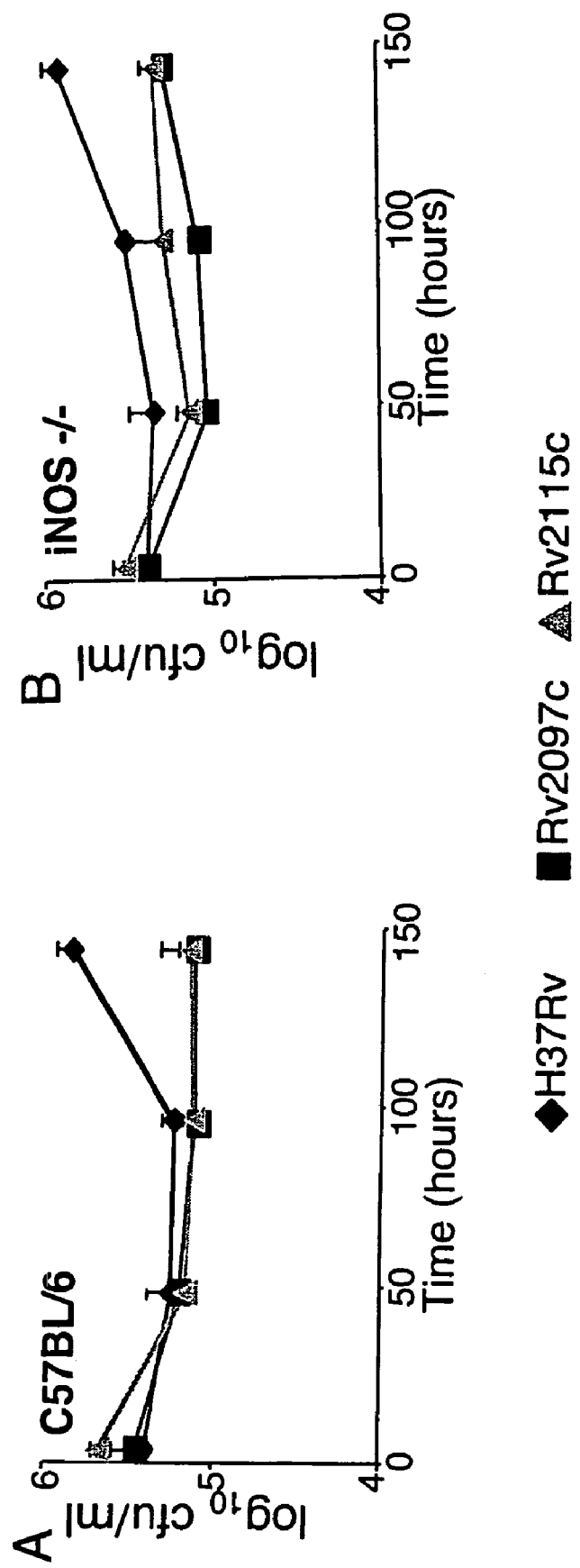
FIGS. 6A-B show the decreased growth and pathology of Rv2115c-mutant Mtb in mice.

Unlike wt Mtb, Rv2115c and Rv2097c mutants failed to grow in resting primary macrophages from wt, as shown in FIG. 6A, or iNOS−/− mice, shown in FIG. 6B. Thus, disruption of Rv2115c and Rv2097c sensitized Mtb to more macrophage-associated stresses than those dependent on iNOS.

Figure 7:
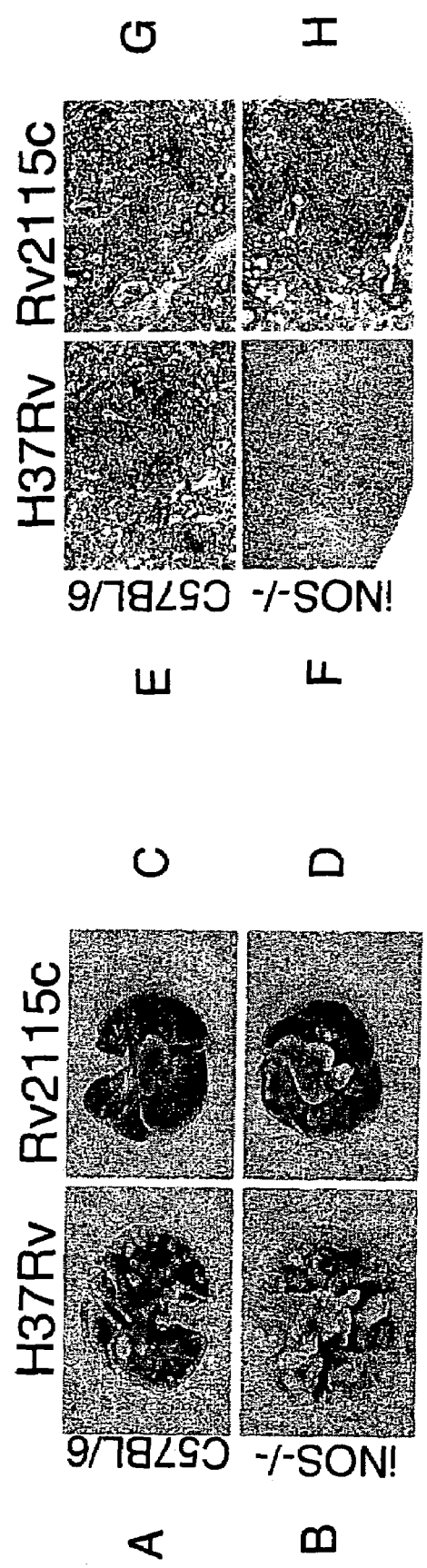
FIGS. 7A-D show lungs of C57BL/6 (wt) and iNOS$^{-/-}$ mice infected by inhalation of wt Mtb or an Rv215c mutant 56 days after aerosol infection.
FIGS. 7E-H are 4× view of sections of the same lungs as FIGS. 7A-D stained with hematoxylin and eosin.

Wt and iNOS−/− mice were infected by inhalation of wt Mtb or an Rv215c mutant. By 8 weeks, *tuberculous* nodules were prominent in the lungs of wt mice infected with wt Mtb, but the Rv215c mutant was markedly attenuated, as shown in FIG. 7A. Mice lacking iNOS suffered nearly complete consolidation of the lungs when infected with wt Mtb. The Rv2115c mutant caused an intermediate degree of gross pathology in lungs of iNOS−/− mice (FIG. 7A). All iNOS−/− mice infected with wt Mtb succumbed by week 9, while the other three experimental groups remained alive at week 31, shown in FIG. 8A-B. Histologically, the Rv2115c mutant caused minimal pneumonitis in wt mice and more pneumonitis in iNOS−/− mice, as shown in FIGS. 7A-B and FIGS. 9A-B. However, only wt Mtb caused necrosis, and only in iNOS−/− mice, as shown in FIG. 7F. By 8-9 weeks, 1-4 $\log_{10}$ fewer CFU of the Rv2115c mutant than the wt strain of Mtb were recovered from lungs, spleens, and livers of mice of both strains. The deficit in viable bacteria in each organ was reversed by complementing the Mtb mutant with a single copy of the wt allele of Rv2115c, as shown in FIGS. 10A-F. Thus, despite its normal growth in log and stationary phases in culture, Mtb lacking Rv2115c was far less fit than wt Mtb to grow in mice, to elicit pathology, and to kill the host. The decreased ability of the Rv2115c mutant to cause pathologic changes in the lungs was compensated in part by genetic inactivation of mouse iNOS. In sum, Mtb needs Rv2115c in order to withstand iNOS as well as other stresses imposed by the mammalian host.

Figure 11:
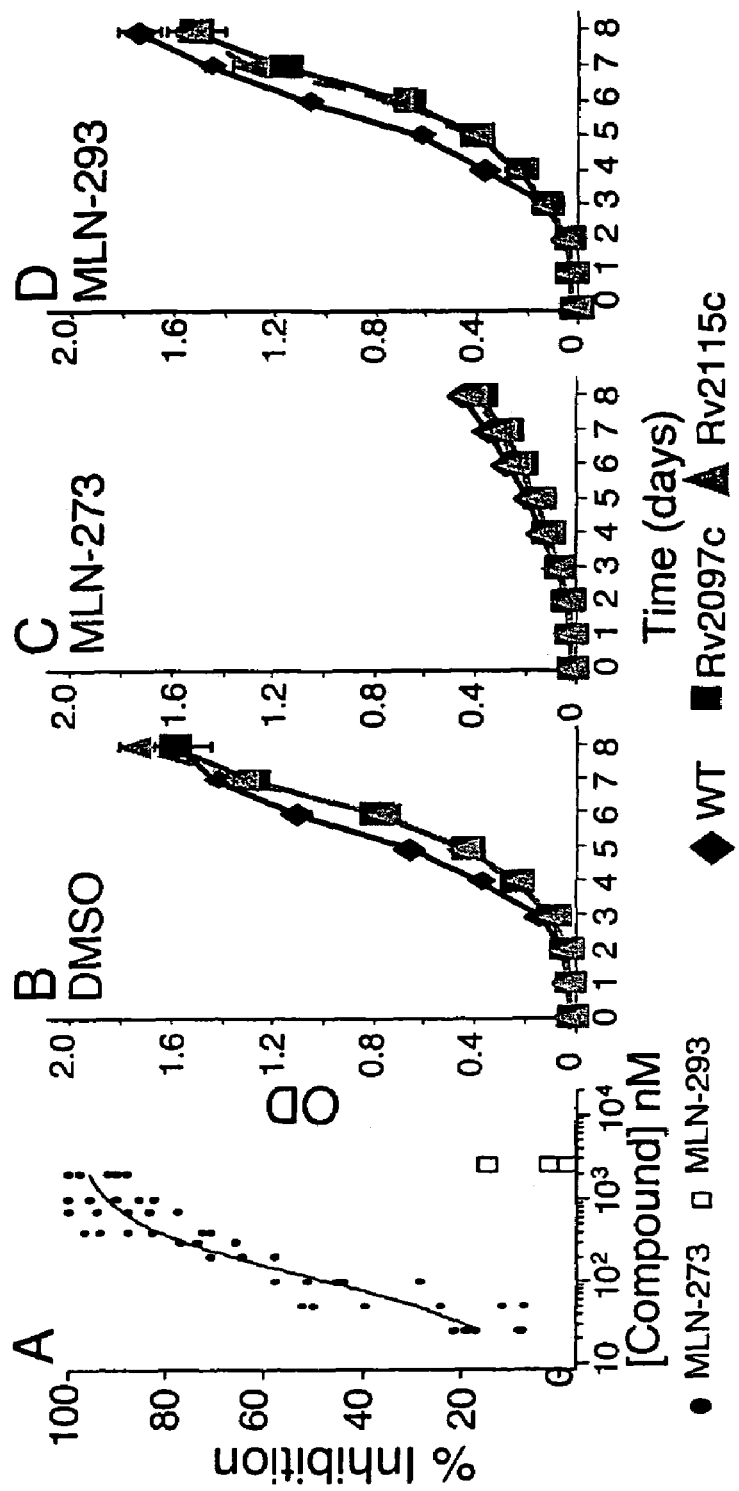
FIGS. 11A-D show reproduction by proteasome inhibitors of the RNI-sensitive phenotype of the Rv2115c and Rv2097c mutants.
Figure 12:
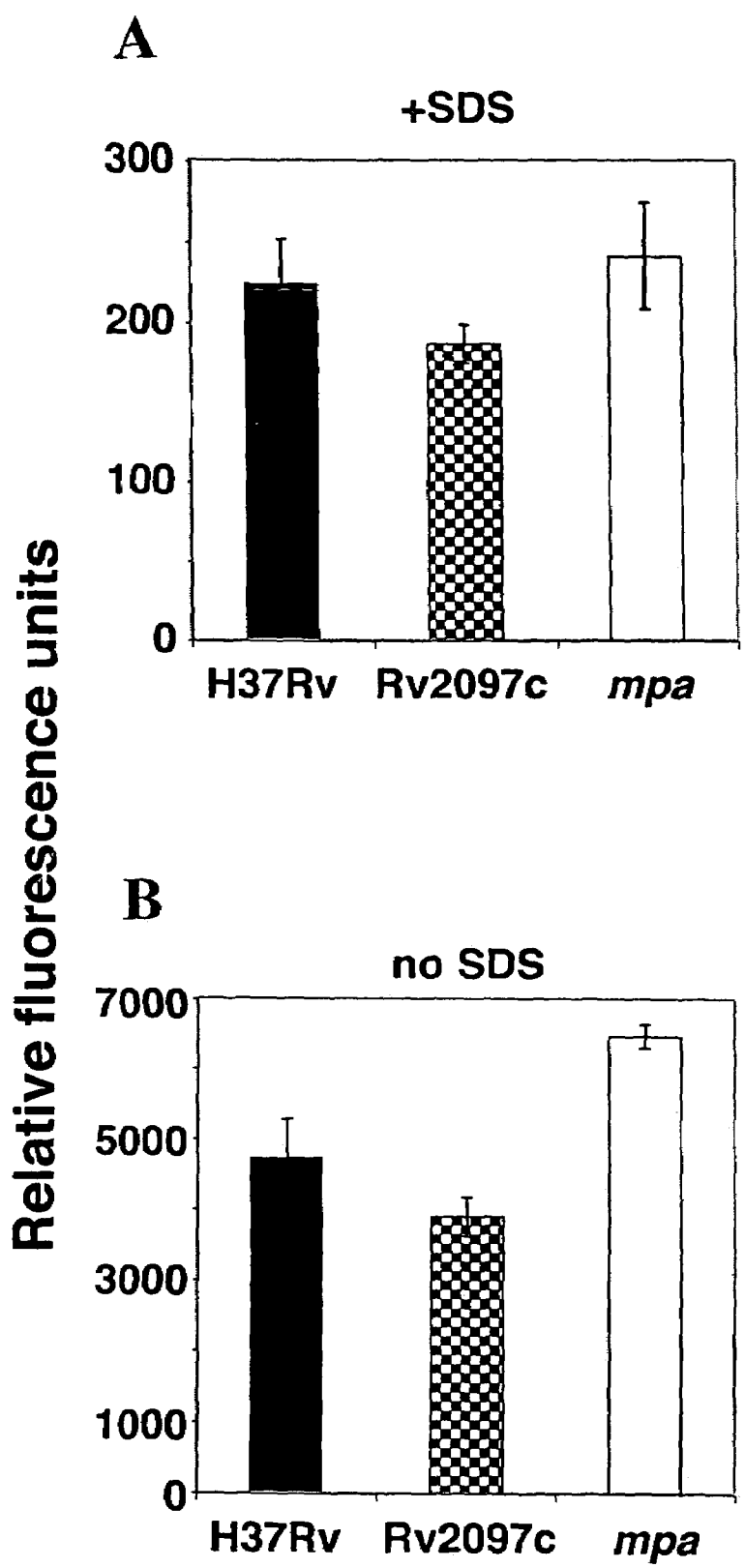
FIGS. 12A-B show comparable proteasomal protease activity in wt Mtb (H37Rv) and mutants in Rv2097c and Rv2115c (mpa), with (FIG. 12A) and without SDS (FIG. 12B).
Figure 13:
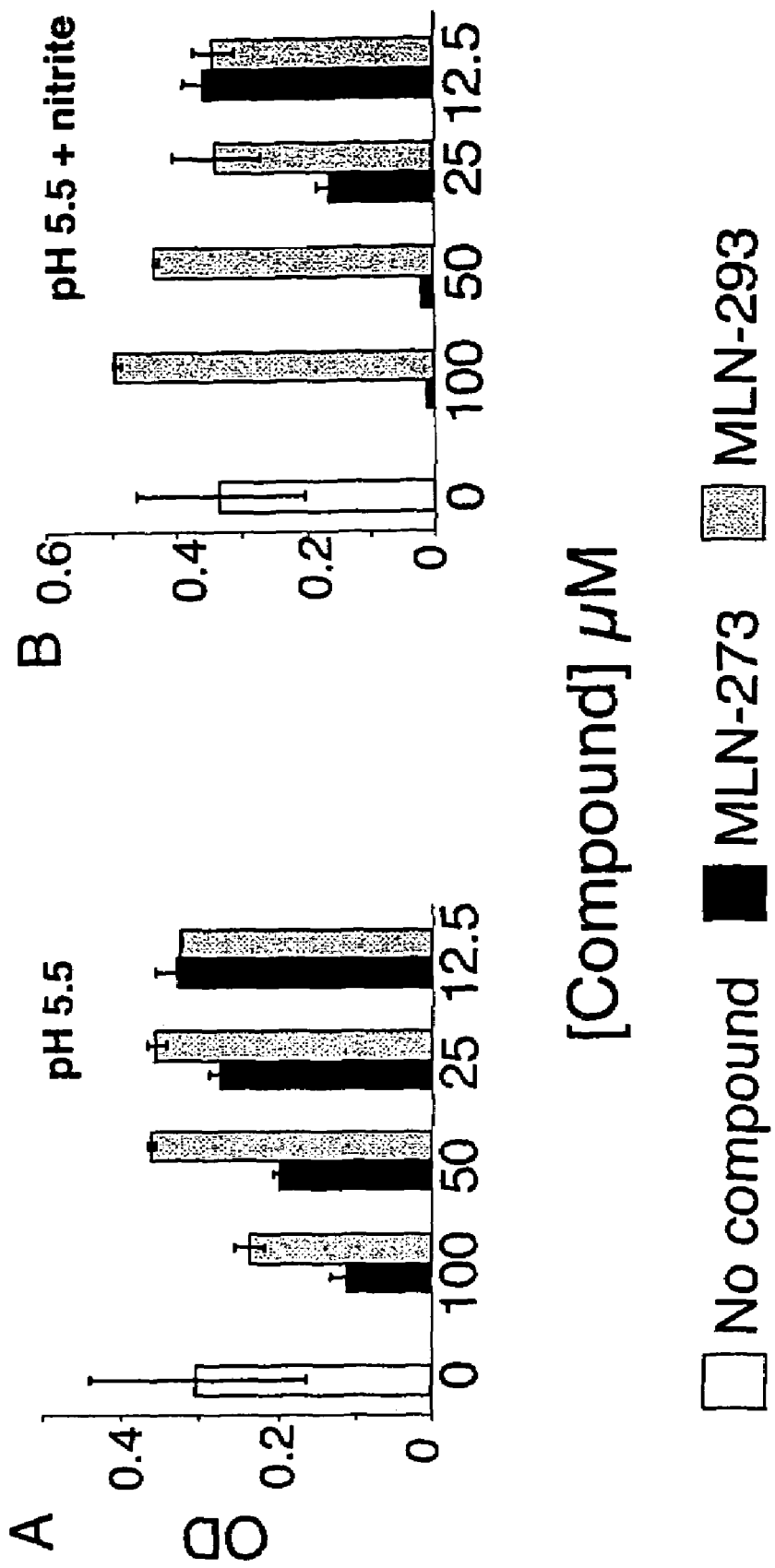
FIGS. 13A-B shows MLN-273 inhibits recovery of wt Mtb from nitrite-mediated injury as assayed in liquid culture. Mtb was incubated with either no compound, MLN-273, or MLN-293 in 7H9-ADNaCl at pH 5.5 with or without 3 mM nitrite. Bacteria were subcultured into fresh 7H9-ADNaCl at pH 6.6. Outgrowth of surviving bacteria was measured by optical density ($A_{580}$).
Figure 14:
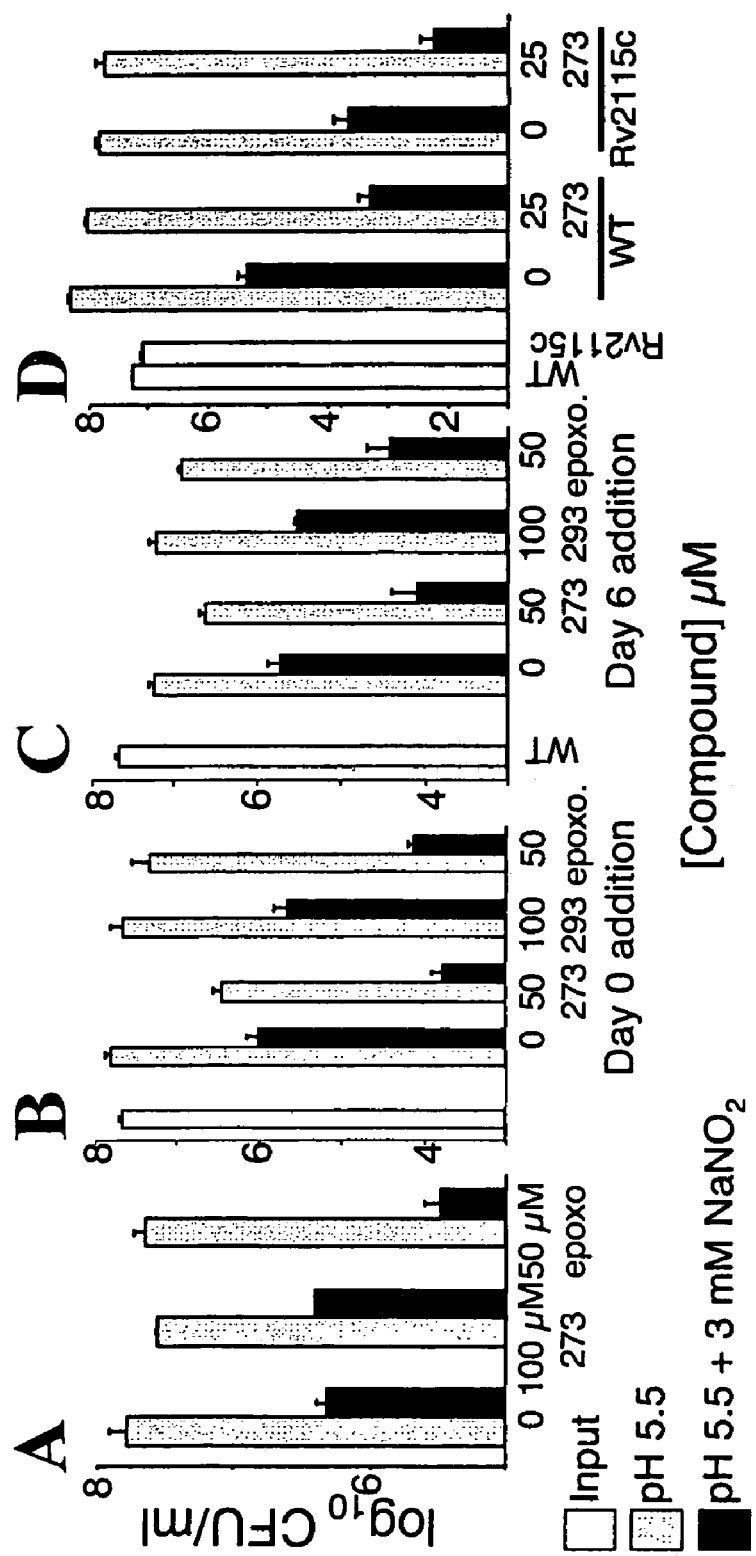
FIGS. 14A-D show the suppressed the growth of these mutants.

Screening found no prcBA mutants, probably because the prcBA operon is necessary for optimal growth or essential in Mtb (Sassetti et al., "Genes Required for *Mycobacterial* Growth Defined by High Density Mutagenesis," *Mol. Microbiol.* 48(1):77-84 (2003), which is hereby incorporated by reference in its entirety), in contrast to its apparent dispensability in *M. smegmatis* (Knipfer et al., "Inactivation of the 20S Proteasome in *Mycobacterium smegmatis*," *Mol. Microbiol.* 25(2):375-83 (1997), which is hereby incorporated by reference in its entirety). As an alternative approach to studying the role of prcBA in Mtb, it was asked if chemical inhibitors of the chymotrypsin-like activity of the eukaryotic proteasome would reproduce the RNI-sensitive phenotype of the Rv2115c and Rv2097c mutants. Indeed, an inhibitor of the human proteasomal protease, N-[4-morpholine]carbonyl-β-[1-naphthyl]-L-alanine-L-leucine boronic acid (MLN-273) (Kisselev et al., "Proteasome Inhibitors: from Research Tools to Drug Candidates," *Chem. Biol.* 8(8):739-758 (2001), which is hereby incorporated by reference in its entirety), potently blocked proteasomal protease activity in Mtb lysates. Its enantiomer, MLN-293, was inactive, as shown in FIG. 11A. Moreover, MLN-273, but not MLN-293 or the vehicle, DMSO, suppressed the growth of Mtb under standard culture conditions, as shown in FIGS. 11B-D. Lysates of the Rv2115c and Rv2097c mutants had normal proteasomal protease activity against the tetrapeptide substrate (FIGS. 12A-B, and MLN-273) and suppressed the growth of these mutants to same extent as for wt Mtb (FIGS. 11B-D). Finally, MLN-273 enhanced the ability of nitrite to suppress outgrowth of Mtb in culture, as shown in FIGS. 13A-B. In survival assays based on growth of Mtb on agar plates, an irreversible proteasomal protease inhibitor, epoxomicin (Kisselev et al., "Proteasome Inhibitors: from Research Tools to Drug Candidates," *Chem. Biol.* 8(8):739-758 (2001), which is hereby incorporated by reference in its entirety), augmented the mycobacteriacidal effect of nitrite, but MLN-273, a reversible inhibitor, did not, as shown in FIG. 14A. In contrast, both MLN-273 and epoxomicin increased the anti-mycobacterial activity of nitrite when Mtb was given time to recover during a four day period of subculture at pH 6.5 in the presence of the inhibitors before being plated, as shown in FIG. 14B. In fact, both compounds were just as effective if added only at the time of the subculture, as shown in FIG. 14C. MLN-273 also augmented the toxicity of nitrite against the Rv2115c mutant, as shown in FIG. 14D. The control compound, MLN-293, had little or no activity under any conditions. Since the proteasomal protease inhibitors acted subsequent to nitrite-mediated injury, they appeared to block the ability of Mtb to recover.

Thus, two chemically distinct proteasome inhibitors produced a phenotype that both mimicked and augmented the effects of mutations in Rv2115c and Rv2097c. This supports the inferences from bioinformatics that Rv2115c and Rv2097c participate in proteasome function and do so at a separate site from the proteasomal protease. Although proteasome regulatory cap structures have not been identified in microbes, Rv2115c and Rv2097c may contribute to an analogous function. Based on its genomic organization and homology to ARC and PAN, it is proposed that Rv2115c be named mpa, for mycobacterial proteasome ATPase. Rv2115c may help unfold proteins and translocate them into the proteolytic core. It is proposed that Rv2097c be named paf for proteasome accessory factor. Rv2097c may recognize a signal on a protein targeted for degradation.

As described above herein, at least six different pathways are individually essential and non-redundant for resistance of Mtb to acidified nitrite. Among these is the proteasome. Thus, one function of the bacterial proteasome is to protect the organism against oxidative or nitrosative stress. The mechanism of protection probably involves the degradation of proteins that are irreversibly oxidized, nitrated, or nitrosated. Inhibition of the Mtb proteasome markedly sensitized the pathogen to bactericidal chemistries of the host. Specific inhibitors of the bacterial proteasome might be useful to sensitize Mtb to the immune system, especially if combined with agents that target one or more of the other RNI-resistance enzymes identified in this screen, such as UvrB. Thus, the most comprehensive approach to targeting the protein cycle in Mtb would include, besides the usual antibiotics directed at the ribosome, antimicrobials directed at GroEL, antimicrobials directed at the proteasomal ATPase, and antimicrobials directed at the proteasomal protease. The latter three used in combination would represent a stunning new approach to antibacterial chemotherapeutics.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A method of treating a prokaryotic pathogen infection in a subject, said method comprising:
   inhibiting the proteolytic activity of a proteasomal core protease in a prokaryotic pathogen by administering an inhibitor of a prokaryotic proteasomal core protease to make the prokaryotic pathogen susceptible to antibacterial host defenses of oxidative stress or nitrosative stress,
   thereby treating a prokaryotic pathogen infection in the subject.

2. The method according to claim 1, wherein the prokaryotic proteasomal core protease is a product of either the prcA gene or the prcB gene.

3. The method according to claim 2, wherein the protease is PrcA.

4. The method according to claim 2, wherein the protease is PrcB.

5. The method according to claim 1, wherein the host defense is reactive nitrogen intermediate-induced stress.

6. The method according to claim 1, wherein the host defense is reactive oxygen intermediate-induced stress.

7. The method according to claim 1, wherein the administering is oral, intradermal, intramuscular, intraperitoneal, intravenous, subcutaneous, or intranasal.

8. The method according to claim 1, wherein the inhibitor of prokaryotic proteasomal core protease activity is selected from the group consisting of epoxomicin and N-[4-morpholine]carbonyl-13-[1-naphthyl]-L-alanine-L-leucine boronic acid.

9. The method according to claim 1, wherein the pathogen is a disease-causing *Mycobacterium*.

10. The method according to claim 9, wherein the disease-causing *Mycobacterium* is selected from the group consisting of *Mycobacterium tuberculosis* and *Mycobacterium leprae*.

11. The method according to claim 1, wherein the subject is a mammal.

12. The method according to claim 11, wherein the mammal is human.

* * * * *

SEQUENCE LISTING

```
<160> NUMBER OF SEQ ID NOS: 1

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence:  Synthetic
      Peptide Domain of Inhibitor Protein

<400> SEQUENCE: 1

Leu Leu Val Tyr
 1
```